United States Patent
Dellinger et al.

(10) Patent No.: US 11,524,022 B2
(45) Date of Patent: *Dec. 13, 2022

(54) USE OF NICOTINAMIDE RIBOSIDE, NICOTINIC ACID RIBOSIDE, AND NICOTINAMIDE MONONUCLEOTIDE, REDUCED NICOTINYL COMPOUNDS, AND NICOTINOYL COMPOUND DERIVATIVES IN INFANT FORMULA FOR HEALTHY DEVELOPMENT

(71) Applicant: ChromaDex, Inc., Irvine, CA (US)

(72) Inventors: Ryan Dellinger, Azusa, CA (US); Troy Rhonemus, Mission Viejo, CA (US); Mark Morris, Irvine, CA (US); Dietrich Conze, Garrett Park, MD (US); Amy Boileau, Libertyville, IL (US)

(73) Assignee: ChromaDex Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/114,864

(22) Filed: Dec. 8, 2020

(65) Prior Publication Data

US 2021/0228604 A1    Jul. 29, 2021

Related U.S. Application Data

(63) Continuation of application No. 15/488,215, filed on Apr. 14, 2017, now Pat. No. 10,857,172.

(60) Provisional application No. 62/322,460, filed on Apr. 14, 2016.

(51) Int. Cl.
| | |
|---|---|
| *A61K 31/706* | (2006.01) |
| *A61K 31/51* | (2006.01) |
| *A23L 33/10* | (2016.01) |
| *A61K 31/4415* | (2006.01) |
| *A61K 31/455* | (2006.01) |
| *A61K 31/525* | (2006.01) |
| *A61K 31/7064* | (2006.01) |
| *A23L 33/19* | (2016.01) |
| *A23L 33/00* | (2016.01) |
| *A23L 33/15* | (2016.01) |
| *A61K 47/42* | (2017.01) |
| *A61K 45/06* | (2006.01) |

(52) U.S. Cl.
CPC ............ *A61K 31/706* (2013.01); *A23L 33/10* (2016.08); *A23L 33/15* (2016.08); *A23L 33/19* (2016.08); *A23L 33/30* (2016.08); *A23L 33/40* (2016.08); *A61K 31/4415* (2013.01); *A61K 31/455* (2013.01); *A61K 31/51* (2013.01); *A61K 31/525* (2013.01); *A61K 31/7064* (2013.01); *A61K 45/06* (2013.01); *A61K 47/42* (2013.01); *A23V 2002/00* (2013.01)

(58) Field of Classification Search
CPC ...... A61K 31/706; A61K 31/455; A23L 33/40
See application file for complete search history.

(56) References Cited

U.S. PATENT DOCUMENTS

| | | |
|---|---|---|
| 2006/0002914 A1 | 1/2006 | Milbrandt et al. |
| 2007/0117765 A1 | 5/2007 | Sauve et al. |
| 2009/0311379 A1 | 12/2009 | Petschow et al. |
| 2010/0104686 A1 | 4/2010 | Rosales et al. |
| 2010/0104721 A1 | 4/2010 | Legan et al. |
| 2010/0104727 A1 | 4/2010 | Gonzalez et al. |
| 2015/0237902 A1 | 8/2015 | Rosado et al. |
| 2017/0204131 A1 | 7/2017 | Szczepankiewicz et al. |

FOREIGN PATENT DOCUMENTS

| | | |
|---|---|---|
| WO | WO2007061798 A2 | 5/2007 |
| WO | 2014042503 A1 | 3/2014 |

OTHER PUBLICATIONS

Chi, Yuling et al., Current Opinion in Clinical Nutrition and Metabolic Care, "Nicotinamide riboside, a trace nutrient in foods, is a Vitamin B3 with effects on energy metabolism and neuroprotection", 2013, vol. 16, issue 6, pp. 657-661 (Year: 2013).*
Rios-Covian, D. et al. "Intestinal Short Chain Fatty Acids and their Link with Diet and Human Health," Frontiers in Microbiology, Feb. 2016, vol. 7, Article 185, 9 pages.
"ChromaDex(R) Introduces NIAGEN(TM)—The First and Only Commercially Available Nicotinamide Riboside." Press Release [online]. Chromadex Corporation, May 29, 2013 [retrieved on Jun. 14, 2017]. Retrieved from the Internet: <URL: http://investors.chromadex.com/phoenix.zhtml?c=212121&p=irol-newsArticle&ID=1824773. line 2, para 2.
M.K. Horwitt, Niacin-Tryptophan Relationships in the Development of Pellagra, 3 Am. J. Clinical Nutrition 244 (1955).
M.K. Horwitt et al., "Niacin-tryptophan relationships for evaluating niacin equivalents," 34 Am. J. Clinical Nutrition 423 (1981).
"6. Niacin," in Institute of Medicine, Food & Nutrition Board, Dietary Reference Intakes for Thiamin, Riboflavin, Niacin, Vitamin B6, Folate, Vitamin B12, Pantothenic Acid, Biotin, and Choline (1998).
Awel Bieganowski & Charles Brenner, Discoveries of Nicotinamide Riboside as a Nutrient and Conserved NRK Genes Establish a Preiss-Handler Independent Route to NAD+ in Fungi and Humans, 117 Cell 495 (2004).

(Continued)

*Primary Examiner* — Bahar Craigo
(74) *Attorney, Agent, or Firm* — Amin Talati Wasserman LLP; George M. Carrera, Jr.; Valerie Meymeyer-Tynkov

(57) ABSTRACT

Methods for delivering at least one compound selected from nicotinamide riboside (NR), nicotinic acid riboside (NAR), and nicotinamide mononucleotide (NMN), derivatives thereof, or salts thereof, in combination with at least one of thiamine (vitamin B1), riboflavin (vitamin B2), niacin (vitamin B3), and pyridoxine (vitamin B6), to an infant human subject in need of said compound or compounds are provided.

22 Claims, 12 Drawing Sheets

(56) References Cited

OTHER PUBLICATIONS

"Niacin: Nicotinic Acid, Nicotinamide, and Inositol Hexanicotinate," in John N. Hathcock, Vitamin & Mineral Safety (Douglas MacKay et al., eds., 3d ed., Council for Responsible Nutrition (CRN) 2014), available at http://www.crnusa.org/sites/default/files/files/resources/CRN-SafetyBook-3rdEdition-2014-fullbook.pdf.

European Food Safety Authority, "Draft Scientific Opinion on Dietary Reference Values for niacin," EFSA J. (2014), available at http://www.efsa.europa.eu/efsajournal/.

Carles Canto, et al., "NAD+ Metabolism and the Control of Energy Homeostasis: A Balancing Act between Mitochondria and the Nucleus," 22 Cell Metabolism 31 (2015).

National Institutes of Health, U.S. Dep't of Agriculture, "Unit Conversions," https://dietarysupplementdatabase.usda.nih.gov/Conversions.php (last updated Aug. 14, 2017).

Yuling Chi & Anthony A. Sauve, Nicotinamide riboside, a trace nutrient in foods, is a Vitamin B3 with effects on energy metabolism and neuroprotection, 16 Curr. Opinion in Clin. Nutrition & Metabolic Care 657 (2013).

Zoltan Benyo, et al., GPR109A (PUMA-G/HM74A) mediates nicotinic acid-induced flushing, 115 J. Clinical Investigation 3634 (2005).

Carles Canto, et al., The NAD+ Precursor Nicotinamide Riboside Enhances Oxidative Metabolism and Protects against High-Fat Diet-Induced Obesity, 15 Cell Metabolism 838 (2012).

EFSA Panel on Dietetic Products, et al., "Safety of D-ribose as a novel food pursuant to Regulation (EU) 2015/2283," EFSA Journal, Scientific Opinion (2018); 16(5):5265 (pp. 1-28).

Randy W. Johnson, et al., "Pyridine Nucleotide Chemistry. A New Mechanism for the Hydroxide-Catalyzed Hydrolysis of the Nicotinamide-Glycosyl Bond," J. American Chemical Society (1988); 110: 2257-2263.

Samuel AJ Trammell et al., "Nicotinamide Riboside is a Major NAD+ Precursor Vitamin in Cow Milk"; The Journal of Nutrition (2016); doi: 10.3945/jn. 116.230078.

M. Gross and N. Zollner; "Serum levels of glucose, insulin, and C-peptide during long-term D-ribose administration in man," Klinische Wochenschrift 69(1): 31-36 (1991); https://link.springer.com/article/10.1007/BF01649054.

Xiaonan Han et al., "NAD+ Ameliorates Inflammation-Induced Epithelial Barrier Dysfunction in Cultured Enterocytes and Mouse Ileal Mucosa" J. Pharmacol. Exper. Therapeut. 307(2):443-449 (2003).

Capuzzi, D. M. et al., Current Atherosclerosis Reports, "Niacin Dosing: Relationship to Benefits and Adverse Effects", 2000, vol. 2, pp. 64-71 (Year: 2000).

Yang, T. et al., J. Med. Chem., "Syntheses of Nicotinamide Riboside and Derivatives: Effective Agents for Increasing Nicotinamide Adenine Dinucleotide Concentralions in Mammalian Cells", 2007, vol. 50, pp. 6458-6461 (Year: 2007).

Bogan, K. L. et al., Annu. Rev. Nutr., "Nicotinic Acid, Nicotinamide, and Nicotinamide Riboside: A Molecular Evaluation of NAO+ Precursor Vitamins in Human Nutrition", 2008, vol. 28, pp. 115-130.

Australian Health and Medical Research Council (NHMRC), 2006, "Niacin", pp. 79-84.

ChromaDex® Announces Deal for Its Recently Launched Niagen™ Nicotinamide Riboside With Thorne Research, Cision PR newswire. <https://www.prnewswire.com/news-releases/chromadex-announces-deal-for-its-recently-launched-niagen-nicotinamide-riboside-with-thorne-research-214585981.html> (Jul. 8, 2013) (8 pages).

* cited by examiner

USE OF NICOTINAMIDE RIBOSIDE, NICOTINIC ACID RIBOSIDE, AND NICOTINAMIDE MONONUCLEOTIDE, REDUCED NICOTINYL COMPOUNDS, AND NICOTINOYL COMPOUND DERIVATIVES IN INFANT FORMULA FOR HEALTHY DEVELOPMENT

This application is a continuation of U.S. application Ser. No. 15/488,215 filed on Apr. 14, 2017 which claims the benefit of U.S. Provisional Application No. 62/322,460, filed on Apr. 14, 2016. The disclosures of each of the prior applications are hereby incorporated by reference herein in their entireties.

TECHNICAL FIELD

In certain embodiments, the present invention relates to methods for delivering at least one compound selected from nicotinamide riboside ("NR"), nicotinic acid riboside ("NAR"), and nicotinamide mononucleotide ("NMN"), derivatives thereof, or salts thereof, to an infant human subject in need of said compound or compounds. In further embodiments, the invention relates to methods for delivering at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6), to an infant human subject in need of said compound or compounds. In further embodiments, the invention relates to methods for treating and/or preventing symptoms, diseases, disorders, or conditions associated with, or having etiologies involving, vitamin B3 deficiency and/or that would benefit from increased mitochondrial activity in an infant human subject. In further embodiments, the invention relates to methods for promoting the growth of beneficial species of bacteria in the gut of an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6). In further embodiments, the invention relates to methods for promoting the gut health of an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6). In further embodiments, the invention relates to methods for reducing gastrointestinal inflammation in an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6).

BACKGROUND

Vitamin B3, and other B-vitamins such as thiamine (vitamin B1), riboflavin (vitamin B2), and pyridoxine (vitamin B6) are extracted in their coenzyme forms from foodstuffs. During digestion, the coenzymes are catabolized to the free circulating vitamins, which are then passively or actively transported across membranes, and salvaged intracellularly to their respective cofactors. Mammals are entirely reliant on a dietary source of vitamin B1 and heavily dependent on the dietary supply of vitamins B2, B3, and B6. Of note, acute deficiencies in vitamin B1 and vitamin B3 affect identical organs, with identical outcomes if left untreated: dementia and death.

During normal healthy development, it is critical that an infant receive the proper essential nutrients. Human breast milk is the most suitable for delivery of these essential nutrients as long as the maternal diet is adequate and human breast milk is in adequate supply. Therefore, knowledge of the composition of human breast milk, coupled with the nutrient intakes of healthy young infants, is essential to understanding nutritional requirements of human babies. This knowledge is also key to producing appropriate substitutes (i.e., infant formula) when human breast milk is not fed to an infant, irrespective of the reason for not feeding human breast milk to an infant.

Water-soluble vitamins are a vital component of human milk. However, the vitamin content of human milk can be affected by numerous factors, chief among them the nutritional status of the mother. In general, when maternal vitamin intakes are low, this corresponds to low vitamin content in the breast milk. See M. F. Picciano, *Human Milk: Nutritional Aspects of a Dynamic Food*, 74 NEONATOLOGY 84 (1998). Thus, these women and infants would be candidates for supplementation with vitamins and/or infant formula. Vitamin B3s are among the essential water soluble vitamins found naturally in human breast milk. See Picciano, 1998. Vitamin B3s, along with the essential amino acid tryptophan, play an essential role in biology as nicotinamide adenine dinucleotide ("NAD$^+$") precursors.

The dietary vitamin B3, which encompasses nicotinamide ("Nam" or "NM"), nicotinic acid ("NA"), and nicotinamide riboside ("NR"), is a precursor to the coenzyme nicotinamide adenine nucleotide (NAD+), its phosphorylated parent ("NADP+" or "NAD(P)+"), and their respective reduced forms ("NADH" and "NADPH," respectively).

Eukaryotes can synthesize NAD$^+$ de novo via the kynurenine pathway from tryptophan. See W. A. Krehl et al., *Growth-retarding Effect of Corn in Nicotinic Acid-Low Rations and its Counteraction by Tryptophane*, 101 SCIENCE 489 (1945); Gunther Schutz & Philip Feigelson, *Purification and Properties of Rat Liver Tryptophan Oxygenase*, 247 J. BIOL. CHEM. 5327 (1972); each of which is incorporated by reference herein in its entirety. The kynurenine pathway is a de novo pathway that originates from tryptophan. Through the sequential enzymatic action of tryptophan 2,3-dioxygenase ("TDO"), indoleamine 2,3-dioxygenase ("IDO"), kynurenine formamidase ("KFase"), kynurenine 3-hydroxylase ("K3H"), kynureninase, and 3-hydroxyanthranylate 3,4-dioxygenase ("3HAO"), tryptophan ("Trp") is converted to quinolinic acid ("QA"). See Javed A. Khan et al., *Nicotinamide adenine dinucleotide metabolism as an attractive target for drug discovery*, 11 EXPERT OPIN. THER. TARGETS 695 (2007), incorporated by reference herein in its entirety. Quinolinic acid (QA) is converted to nicotinic acid mononucleotide ("NaMN") through the action of quinolinic phosphoribosyltransferase ("QAPRTase"). See Khan et al., 2007.

The de novo kynureninase pathway, which produces nicotinic acid mononucleotide (NaMN) from quinolinic acid (QA), feeds into the well-established Preiss-Handler pathway, in which nicotinic acid mononucleotide (NaMN) is an intermediate. The Preiss-Handler pathway is a salvage pathway that starts with the conversion of nicotinic acid (NA) to nicotinic acid mononucleotide (NaMN), catalyzed by the enzyme nicotinate phosphoribosyltransferase ("NAPRT" or "NAPRTase"). Nicotinic acid mononucleotide (NaMN) is then adenylylated to form nicotinic acid adenine dinucleotide ("NaAD"), catalyzed by the enzyme nicotinic acid/nicotinamide mononucleotide adenylyltransferase ("NMNAT"). Nicotinic acid adenine dinucleotide (NaAD) is in turn amidated to form nicotinamide adenine dinucleotide ($NAD^+$), catalyzed by the enzyme nicotinamide adenine dinucleotide synthetase ("NADS"). Nicotinamide (Nam or NM), which is a breakdown product of NAD+, can be converted to nicotinic acid (NA), catalyzed by the enzyme nicotinamide deamidase ("NM deamidase"). See Jack Preiss & Philip Handler, *Biosynthesis of Diphosphopyridine Nucleotide*, 233 J. BIOL. CHEM. 493 (1958), incorporated by reference herein in its entirety. See also, Khan et al., 2007.

Another salvage pathway can convert nicotinamide (Nam or NM), the breakdown product of nicotinamide adenine dinucleotide ($NAD^+$), into nicotinamide mononucleotide ("NMN"), by the action of the coenzyme nicotinamide phosphoribosyltransferase ("NMPRT" or "NMPRTase"). Nicotinamide mononucleotide (NMN) can then be directly converted into nicotinamide adenine dinucleotide (NAD+) by nicotinic acid/nicotinamide mononucleotide adenylyltransferase (NMNAT). Alternatively, nicotinamide (Nam or NM) can be deamidated to form nicotinic acid (NA), which can then enter the Preiss-Handler pathway. Analysis of genome sequences suggests that the above two salvage pathways are often mutually exclusive; many organisms contain either NM deamidase or NMPRTase. See Khan et al., 2007.

Nicotinamide riboside (NR) can also be used as a precursor for nicotinamide adenine dinucleotide ($NAD^+$) biosynthesis, and nicotinamide riboside kinase ("NRK") catalyzes the phosphorylation of nicotinamide riboside (NR) to produce nicotinamide mononucleotide (NMN). See Khan et al., 2007.

Notably, nicotinamide riboside (NR) has not been considered a precursor to nicotinamide adenine dinucleotide ($NAD^+$) via the Preiss-Handler salvage pathway, or via conversion into nicotinic acid mononucleotide (NaMN) or nicotinic acid adenine dinucleotide (NaAD) as intermediates. Instead, the biosynthetic pathway for nicotinic acid riboside (NAR) is known to proceed directly to nicotinic acid mononucleotide (NaMN), then nicotinic acid adenine dinucleotide (NaAD), and ultimately to form $NAD^+$.

Nicotinamide adenine dinucleotide ($NAD^+$) is an enzyme co-factor and the central reduction-oxidation coenzyme that is essential for the function of several enzymes related to reduction-oxidation reactions and cellular energy metabolism. See Peter Belenky et al., *$NAD^+$ metabolism in health and disease*, 32 TRENDS IN BIOCHEMICAL SCIS. 12 (2007); Katrina L. Bogan & Charles Brenner, *Nicotinic Acid, Nicotinamide, and Nicotinamide Riboside: A Molecular Evaluation of $NAD^+$ Precursor Vitamins in Human Nutrition*, 28 ANNUAL REV. OF NUTRITION 115 (2008); each of which is incorporated by reference herein in its entirety. Nicotinamide adenine dinucleotide ($NAD^+$) functions as an electron carrier or hydride group acceptor in cell metabolism, forming reduced nicotinamide adenine dinucleotide (NADH), with concomitant oxidation of metabolites derived from carbohydrates, amino acids, and fats. See Bogan & Brenner, 2008. The $NAD^+$/NADH ratio controls the degree to which such reactions proceed in oxidative versus reductive directions. Whereas fuel oxidation reactions require $NAD^+$ as a hydride acceptor, the processes of gluconeogenesis, oxidative phosphorylation, ketogenesis, detoxification of reactive oxygen species, and lipogenesis require reduced co-factors, NADH and NADPH, to act as hydride donors.

In addition to its role as a coenzyme, $NAD^+$ is the consumed substrate, and thus activator, of enzymes such as: poly-ADP-ribose polymerases ("PARPs"); sirtuins, a family of protein deacetylases that have been implicated in metabolic function and extended lifespan in lower organisms; and cyclic ADP-ribose synthetases. See Laurent Mouchiroud et al., *The $NAD^+$/Sirtuin Pathway Modulates Longevity through Activation of Mitochondrial UPR and FOXO Signaling*, 154 CELL 430 (2013), incorporated by reference herein in its entirety. See also Belenky et al., 2006. The co-enzymatic activity of $NAD^+$, together with the tight regulation of its biosynthesis and bioavailability, makes it an important metabolic monitoring system that is clearly involved in the aging process.

Once converted intracellularly to NADP+, vitamin B3 is used as a co-substrate in two types of intracellular modifications, which control numerous essential signaling events (adenosine diphosphate ribosylation and deacetylation), and is a cofactor for over 400 reduction-oxidation enzymes, thus controlling metabolism. This is demonstrated by a range of metabolic endpoints including the deacetylation of key regulatory proteins, increased mitochondrial activity, and oxygen consumption. Critically, the NADPH-cofactor family can promote mitochondrial dysfunction and cellular impairment if present in sub-optimal intracellular concentrations. Vitamin B3 deficiency yields to evidenced compromised cellular activity through $NAD^+$ depletion, and the beneficial effect of additional $NAD^+$ bioavailability through nicotinic acid (NA), nicotinamide (Nam or NM), and nicotinamide riboside (NR) supplementation is primarily observed in cells and tissues where metabolism and mitochondrial function had been compromised.

In reduction-oxidation reactions, the nucleotide structures of $NAD^+$, NADH, NADP+, and NADPH are preserved. In contrast, PARP, sirtuin, and cyclic ADP-ribose synthetase activities hydrolyze the glycosidic linkage between the nicotinamide (Nam or NM) and the ADP-ribosyl moieties of $NAD^+$ to signal DNA damage, alter gene expression, control post-translational modifications, and regulate calcium signaling.

In animals, $NAD^+$-consuming activities and cell division necessitate ongoing $NAD^+$ synthesis, either through the de novo pathway that originates with tryptophan, or via the salvage pathways from $NAD^+$-precursor vitamins nicotinamide (Nam or NM), nicotinic acid (NA), and nicotinamide riboside (NR). See Bogan & Brenner, 2008. Dietary $NAD^+$ precursors, which include tryptophan and the three $NAD^+$-precursor vitamins, prevent pellagra, a disease characterized by dermatitis, diarrhea, and dementia. The beneficial effect of additional $NAD^+$ bioavailability through nicotinamide (Nam or NM), nicotinic acid (NA), and nicotinamide riboside (NR) supplementation is primarily observed in cells and tissues where metabolism and mitochondrial function had been compromised.

Interestingly, supplementation with nicotinic acid (NA) with nicotinamide (Nam or NM), while critical in acute vitamin B3 deficiency, does not demonstrate the same physiological outcomes compared with that of nicotinamide riboside (NR) supplementation, even though, at the cellular level, all three metabolites are responsible for $NAD^+$ biosynthesis. This emphasizes the complexity of the pharmacokinetics and bio-distribution of B3-vitamin components. The bulk of intracellular $NAD^+$ is believed to be regenerated via the effective salvage of nicotinamide (Nam or NM), while de novo $NAD^+$ is obtained from tryptophan. See Anthony Rongvaux et al., *Reconstructing eukaryotic NAD metabolism*, 25 BIOESSAYS 683 (2003), incorporated by reference herein in its entirety. These salvage and de novo pathways depend on the functional forms of vitamin B1, B2, and B6 to generate NAD$^+$ via a phosphoriboside pyrophosphate intermediate. Nicotinamide riboside (NR) is the only form of vitamin B3 from which NAD$^+$ can be generated in a manner independent of vitamin B1, B2, and B6, and the salvage pathway using NR for the production of NAD$^+$ is expressed in most eukaryotes.

Thiamine (vitamin B1), riboflavin (vitamin B2), niacin (vitamin B3), and pyridoxine (vitamin B6) are salvaged from food and converted back intracellularly to their respective, bioactive forms: Thiamine DiPhosphate ("ThDP"); Flavin Adenine Dinucleotide ("FAD"); Nicotinamide Adenine Dinucleotide (NAD$^+$); and PyridoxaL Phosphate ("PLP"). The conversion of vitamins B1, B2, and B6 to ThDP, FAD, and PLP, respectively, is ATP-dependent. Two of the three salvage pathways that convert vitamin B3 to NAD$^+$ are dependent on ThDP (B1), with the de novo production of NAD$^+$ from tryptophan depending on the bioactive forms of vitamins B1, B2, and B6. The vitamin B1 dependency comes from the fact that ThDP (B1) is cofactor for the transketolases involved in the biosynthesis of phosphoriboside pyrophosphate, an essential substrate in these aforementioned NAD$^+$ salvage and de novo pathways. The most recently identified, yet so far believed redundant, third NAD$^+$ salvage pathway, the Nicotinamide Riboside (NR) dependent NAD$^+$ biosynthetic pathway, does not require phosphoriboside pyrophosphate and is independent of vitamins B1, B2, and B6.

Though nicotinamide riboside (NR) is present in milk, the cellular concentrations of NAD$^+$, NADH, NADP$^+$, and NADPH are much higher than those of any other NAD$^+$ metabolites, such that dietary NAD$^+$ precursor vitamins are largely derived from enzymatic breakdown of NAD$^+$. See Pawel Bieganowski & Charles Brenner, *Discoveries of Nicotinamide Riboside as a Nutrient and Conserved NRK Genes Establish a Preiss-Handler Independent Route to NAD$^+$ in Fungi and Humans*, 117 CELL 495 (2002); Charles Evans et al., *NAD$^+$ metabolite levels as a function of vitamins and calorie restriction: evidence for different mechanisms of longevity*, 10 BMC CHEM. BIOL. 2 (2010); Samuel A. J. Trammell & Charles Brenner, *Targeted, LCMS-Based Metabolomics for Quantitative Measurement of NAD$^+$ Metabolites*, 4 COMPUTATIONAL & STRUCTURAL BIOTECH. J. 1 (2013); each of which is incorporated by reference herein in its entirety. Put another way, though milk is a source of nicotinamide riboside (NR), the more abundant sources of nicotinamide riboside (NR), nicotinamide (Nam or NM), and nicotinic acid (NA) are any whole foodstuffs in which cellular NAD$^+$ is broken down to these compounds. Human digestion and the microbiome play roles in the provision of these vitamins in ways that are not fully characterized.

Different tissues maintain NAD$^+$ levels through reliance of different biosynthetic routes. See Federica Zamporlini et al., *Novel assay for simultaneous measurement of pyridine mononucleotides synthesizing activities allow dissection of the NAD$^+$ biosynthetic machinery in mammalian cells*, 281 FEBS J. 5104 (2014); Valerio Mori et al., *Metabolic Profiling of Alternative NAD Biosynthetic Routes in Mouse Tissues*, 9 PLOS ONE e113939 (2014); each of which is incorporated by reference herein in its entirety. Because NAD$^+$-consuming activities frequently occur as a function of cellular stresses and produce nicotinamide (Nam or NM), the ability of a cell to salvage nicotinamide (Nam or NM) into productive NAD$^+$ synthesis through nicotinamide phosphoribosyltransferase ("NAMPT") activity versus methylation of nicotinamide (Nam or NM) to N-methylnicotinamide ("MeNam") regulates the efficiency of NAD$^+$-dependent processes. See Charles Brenner, *Metabolism: Targeting a fat-accumulation gene*, 508 NATURE 194 (2014); Véronique J. Bouchard et al., *PARP-1, a determinant of cell survival in response to DNA damage*, 31 EXPERIMENTAL HEMATOLOGY 446 (2003); each of which is incorporated by reference herein in its entirety. NAD$^+$ biosynthetic genes are also under circadian control, and both NAMPT expression and NAD$^+$ levels are reported to decline in a number of tissues as a function of aging and overnutrition. See Kathryn Moynihan Ramsey et al., *Circadian Clock Feedback Cycle Through NAMPT-Mediated NAD$^+$ Biosynthesis*, 324 SCIENCE 651 (2009); Yasukazu Nakahata et al., *Circadian Control of the NAD$^+$ Salvage Pathway by CLOCK-SIRT1*, 324 SCIENCE 654 (2009); Jun Yoshino et al., *Nicotinamide Mononucleotide, a Key NAD$^+$ Intermediate Treats the Pathophysiology of Diet-and Age-Induced Diabetes in Mice*, 14 CELL METABOLISM 528 (2011); Ana P. Gomes et al., *Declining NAD$^+$ Induces a Pseudohypoxic State Disrupting Nuclear-Mitochondrial Communication during Aging*, 155 CELL 1624 (2013); Nady Braidy et al., *Mapping NAD$^+$ metabolism in the brain of ageing Wistar rats: potential targets for influencing brain senescence*, 15 BIOGERONTOLOGY 177 (2014); Eric Verdin, *NAD$^+$ in aging, metabolism, and neurodegeneration*, 350 SCIENCE 1208 (2015); each of which is incorporated by reference herein in its entirety.

High-dose nicotinic acid (NA), but not high-dose nicotinamide (Nam or NM), has been used by people for decades to treat and prevent dyslipidemias, though its use is limited by painful flushing. See Joseph R. DiPalma & William S. Thayer, *Use of Niacin as a Drug*, 11 ANNUAL REV. OF NUTRITION 169 (1991); Jeffrey T. Kuvin et al., *Effects of Extended-Release Niacin on Lipoprotein Particle Size, Distribution, and Inflammatory Markers in Patients With Coronary Artery Disease*, 98 AM. J. OF CARDIOLOGY 743 (2006); each of which is incorporated by reference herein in its entirety. Though only approximately 15 milligrams per day of either nicotinic acid (NA) or nicotinamide (Nam or NM) is required to prevent pellagra, pharmacological doses of nicotinic acid (NA) can be as high as 2-4 grams. Despite the >100-fold difference in effective dose between pellagra prevention and treatment of dyslipidemias, the beneficial effects of nicotinic acid (NA) on plasma lipids depend on function of nicotinic acid (NA) as an NAD$^+$-boosting compound. See Belenky et al., 2007. According to this view, sirtuin activation would likely be part of the mechanism because nicotinamide (Nam or NM) is an NAD$^+$ precursor in most cells but is a sirtuin inhibitor at high doses. See Kevin J. Bitterman et al., *Inhibition of Silencing and Accelerated Aging by Nicotinamide, a Putative Negative Regulator of Yeast Sir2 and Human SIRT1*, 277 J. BIOL. CHEM. 45099 (2002), incorporate by reference herein in its entirety. See also Zamporlini et al., 2014; Mori et al., 2014.

As discussed above, the main NAD$^+$ precursors that feed the Preiss-Handler salvage pathway and other salvage pathways are nicotinamide (Nam or NM) and nicotinamide riboside (NR). See Bogan & Brenner, 2008. Further, studies have shown that nicotinamide riboside (NR) is used in a conserved salvage pathway that leads to NAD$^+$ synthesis through the formation of nicotinamide mononucleotide (NMN). Upon entry into the cell, nicotinamide riboside (NR) is phosphorylated by the NR kinases ("NRKs"), generating nicotinamide mononucleotide (NMN), which is then converted to NAD$^+$ by nicotinic acid/nicotinamide mononucleotide adenylyltransferase (NMNAT). See Bogan & Brenner, 2008. Because nicotinamide mononucleotide (NMN) is the only metabolite that can be converted to NAD$^+$ in mitochondria, nicotinamide (Nam or NM) and nicotinamide riboside (NR) are the two candidate NAD$^+$ precursors that can replenish NAD⁺ and thus improve mitochondrial fuel oxidation. A key difference is that nicotinamide riboside (NR) has a direct two-step pathway to NAD⁺ synthesis that bypasses the rate-limiting step of the salvage pathway, nicotinamide phosphoribosyltransferase (NAMPT). Nicotinamide (Nam or NM) requires NAMPT activity to produce NAD⁺. This reinforces the fact that nicotinamide riboside (NR) is a very effective NAD⁺ precursor. Conversely, deficiency in dietary NAD⁺ precursors and/or tryptophan (Trp) causes pellagra. See Bogan & Brenner, 2008. In summary, NAD⁺ is required for normal mitochondrial function, and because mitochondria are the powerhouses of the cell, NAD⁺ is required for energy production within cells.

NAD⁺ was initially characterized as a co-enzyme for oxidoreductases. Though conversions between NAD⁺, NADH, NADP⁺, and NADPH would not be accompanied by a loss of total co-enzyme, it was discovered that NAD⁺ is also turned over in cells for unknown purposes. See Morelly L. Maayan, *NAD⁺-Glycohydrolase of Thyroid Homogenates*, 204 NATURE 1169 (1964), incorporated by reference herein in its entirety. Sirtuin enzymes such as Sir2 of *S. cerevisiae* and its homologs deacetylate lysine residues with consumption of an equivalent of NAD⁺, and this activity is required for Sir2 function as a transcriptional silencer. See S. Imai et al., *Sir2: An NAD-dependent Histone Deacetylase That Connects Chromatin Silencing, Metabolism, and Aging*, 65 COLD SPRING HARBOR SYMPOSIA ON QUANTITATIVE BIOLOGY 297 (2000), incorporated by reference herein in its entirety. NAD⁺-dependent deacetylation reactions are required, not only for alterations in gene expression, but also for repression of ribosomal DNA recombination and extension of lifespan in response to calorie restriction. See Lin et al., *Requirement of NAD and SIR2 for Life-Span Extension by Calorie Restriction in Saccharomyces cerevisiae*, 289 SCIENCE 2126 (2000); Lin et al., *Calorie restriction extends Saccharomyces cerevisiae lifespan by increasing respiration*, 418 NATURE 344 (2002); each of which is incorporated by reference herein in its entirety. NAD⁺ is consumed by Sir2 to produce a mixture of 2'- and 3'-O-acetylated ADP-ribose plus nicotinamide (Nam or NM) and the deacetylated polypeptide. See Anthony A. Sauve et al., *Chemistry of Gene Silencing: the Mechanism of NAD⁺-Dependent Deacetylation Reactions*, 40 BIOCHEMISTRY 15456 (2001), incorporated by reference herein in its entirety. Additional enzymes, including poly(ADP-ribose) polymerases and cADP-ribose synthases are also NAD⁺-dependent and produce nicotinamide (Nam or NM) and ADP-ribosyl products. See Mathias Ziegler, *New functions of a long-known molecule*, 267 FEBS J. 1550 (2000); Alexander Bükle, *Physiology and pathophysiology of poly(ADP-ribosyl)ation*, 23 BIOESSAYS 795 (2001); each of which is incorporated by reference herein in its entirety.

The non-coenzymatic properties of NAD⁺ have renewed interest in NAD⁺ biosynthesis. Based on the ability of nicotinamide riboside (NR) to elevate NAD⁺ synthesis, increase sirtuin activity, and extend lifespan in yeast, nicotinamide riboside (NR) has been employed in mice to elevate NAD⁺ metabolism and improve health in models of metabolic stress. See Peter Belenky et al., *Nicotinamide Ribosides Promotes Sir2 Silencing and Extends Lifespan via Nrk1 and Urh1/Pnp1/Meu1 Pathways to NAD⁺*, 129 CELL 473 (2007), incorporated by reference herein in its entirety. See also Bieganowski & Brenner, 2004. Notably, nicotinamide riboside (NR) allowed mice to resist weight gain on a high-fat diet, and to prevent noise-induced hearing loss. See Carles Cantó et al., *The NAD⁺Precursor Nicotinamide Riboside Enhances Oxidative Metabolism and Protects against High-Fat Diet-Induced Obesity*, 15 CELL METABOLISM 838 (2012); Kevin D. Brown et al., *Activation of SIRT3 by the NAD⁺Precursor Nicotinamide Riboside Protects from Noise-Induced Hearing Loss*, 20 CELL METABOLISM 1059 (2014); each of which is incorporated by reference herein in its entirety. Data indicate that nicotinamide riboside (NR) have been interpreted as depending upon mitochondrial sirtuin activities, though not to the exclusion of nucleocytosolic targets. Andrey Nikiforov et al., *Pathways and Subcellular Compartmentation of NAD Biosynthesis in Human Cells*, 286 J. BIOLOGICAL CHEM. 21767 (2011); Charles Brenner, *Boosting NAD to Spare Hearing*, 20 CELL METABOLISM 926 (2014); Carles Cantó et al., *NAD⁺ Metabolism and the Control of Energy Homeostasis: A Balancing Act between Mitochondria and the Nucleus*, 22 CELL METABOLISM 31 (2015); each of which is incorporated by reference herein in its entirety. Similarly, nicotinamide mononucleotide (NMN), the phosphorylated form of nicotinamide riboside (NR), has been used to treat declining NAD⁺ in mouse models of overnutrition and aging. See J. Yoshino et al., 2011; A. P. Gomes et al., 2013. Because of the abundance of NAD⁺-dependent processes, it is not known to what degree NAD⁺-boosting strategies are mechanistically dependent upon particular molecules such as SIRT1 or SIRT3. In addition, the quantitative effect of nicotinamide riboside (NR) on the NAD⁺ metabolome has not been reported in any system.

Vitamins B1, B2, B3, and B6 are closely intertwined in their biosynthetic pathways, with the maintenance and regeneration of the NADPH intracellular pool depending on the availability of ThDP (vitamin B1), FAD (vitamin B2), and PLP (vitamin B6), along with that of ATP.

ATP is believed to be produced through NAD⁺-dependent OXPHOS and glycolysis, and is necessary for the functionalization of the vitamins B1, B2, and B6 to ThDP, FAD, and PLP, respectively. A shortage of any of these vitamins would impact negatively on the biology of the others.

A healthy, growing infant requires a steady intake of essential nutrients and a key component of that would be an NAD⁺ precursor. A human study examining NAD⁺ levels in human skin tissues demonstrated that the amount of NAD⁺ decreases with age. See Hassina Massudi et al., *Age-associated changes in oxidative stress and NAD⁺metabolism in human tissue*, 7 PUBLIC LIBRARY OF SCIENCE ONE e42357 (2012), which is incorporated by reference herein in its entirety. Thus, human infants have the highest concentrations of NAD⁺ in their skin cells compared to older humans. Specifically, almost three times as much NAD⁺ is present in human newborns as compared to adults thirty to fifty years old. Further, human infants have approximately eight times as much NAD⁺ as compared to adults fifty-one to seventy years old. See Massudi et al., 2012. These results support the idea that human infants naturally need higher NAD⁺ levels during that stage of development.

A rationale for synergy between nicotinamide riboside (NR), nicotinic acid riboside (NAR), and nicotinamide mononucleotide (NMN), derivatives thereof, or salts thereof, and vitamins B1, B2, B3, and B6 is explained herein. Pairing at least one compound selected from nicotinamide riboside (NR), nicotinic acid riboside (NAR), and nicotinamide mononucleotide (NMN), derivatives thereof, or salts thereof, with at least one of vitamins B1, B2, B3, and B6 is hypothesized to act synergistically on the NAD⁺ biosynthetic pathway and have a positive effect. This is due to the fact that vitamins B1, B2, and B6 are required for NAD⁺ biosynthesis through NAMPT-dependent pathways, allowing for the further recycling of nicotinamide (Nam or NM) generated from the NR-produced $NAD^+$. Of all the B3-vitamins, only NR functions independently of NAMPT for $NAD^+$ synthesis, in a mole to mole perspective. See W. Todd Penberthy & James B. Kirkland, *Niacin*, in PRESENT KNOWLEDGE IN NUTRITION 293 (10th ed. 2012; Yuling Chi & Anthony A. Sauve, *Nicotinamide riboside, a trace nutrient in foods, is a vitamin B3 with effects on energy metabolism and neuroprotection*, 16 CURR. OPINION IN CLIN. NUTRITION & METABOLIC CARE 657 (2013); each of which is incorporated by reference herein in its entirety. Additionally, vitamin B2 (FAD precursor) is a key vitamin for mitochondrial fatty acid oxidation and OXPHOS processes. Mitochondrial dysfunction can arise from $FAD/FADH_2$ imbalance or deficiency, and it is hypothesized that pairing vitamin B2 to vitamin B3 NAD-precursors would address multiple pathways of mitochondrial dysfunction.

Therefore, it is hypothesized herein that providing at least one compound selected from nicotinamide riboside (NR), nicotinic acid riboside (NAR), and nicotinamide mononucleotide (NMN), derivatives thereof, or salts thereof, individually or optionally in combination with at least one of vitamins B1, B2, B3, and B6, to a human infant, would supply elevated levels of $NAD^+$ to said human infant. Further, providing said at least one compound selected from nicotinamide riboside (NR), nicotinic acid riboside (NAR), and nicotinamide mononucleotide (NMN), derivatives thereof, or salts thereof, individually or optionally in combination with at least one of vitamins B1, B2, B3, and B6, to a human infant, would be effective in treating and/or preventing symptoms, diseases, disorders, or conditions associated with vitamin B3-deficiency and/or that would benefit from increased mitochondrial activity.

If new methods could be found of providing at least one compound selected from nicotinamide riboside (NR), nicotinic acid riboside (NAR), and nicotinamide mononucleotide (NMN), derivatives thereof, or salts thereof, individually or optionally in combination with at least one of vitamins B1, B2, B3, and B6, to a human infant, this would represent a useful contribution to the art. Furthermore, if new methods could be found of treating and/or preventing symptoms, diseases, disorders, or conditions associated with vitamin B3-deficiency and/or that would benefit from increased mitochondrial activity by providing at least one compound selected from nicotinamide riboside (NR), nicotinic acid riboside (NAR), and nicotinamide mononucleotide (NMN), derivatives thereof, or salts thereof, individually or optionally in combination with at least one of vitamins B1, B2, B3, and B6, to a human infant, this would also represent a useful contribution to the art.

SUMMARY OF THE INVENTION

In certain embodiments, the present disclosure provides methods for delivering at least one compound selected from nicotinamide riboside (NR), nicotinic acid riboside (NAR), and nicotinamide mononucleotide (NMN), derivatives thereof, or salts thereof, to an infant human subject in need of said compound or compounds. In further embodiments, the present disclosure provides methods for delivering at least one compound selected from nicotinamide riboside (NR), nicotinic acid riboside (NAR), and nicotinamide mononucleotide (NMN), derivatives thereof, or salts thereof, in combination with at least one of thiamine (vitamin B1), riboflavin (vitamin B2), niacin (vitamin B3), and pyridoxine (vitamin B6) to an infant human subject in need of said compound or compounds are provided. In further embodiments, the present disclosure provides a method for delivering at least one compound selected from the group consisting of nicotinamide riboside (NR), nicotinic acid riboside (NAR), and nicotinamide mononucleotide (NMN), derivatives thereof, or salts thereof, alone or in combination with at least one of vitamins B1, B2, B3, and B6, to an infant human subject in need of said at least one compound, comprising the steps of: (a) providing an infant formula composition comprising at least one compound selected from the group consisting of nicotinamide riboside (NR), nicotinic acid riboside (NAR), and nicotinamide mononucleotide (NMN), derivatives thereof, or salts thereof, and (b) administering the infant formula composition to the infant human subject. In further embodiments, the present disclosure provides methods for treating and/or preventing symptoms, diseases, disorders, or conditions associated with, or having etiologies involving, vitamin B3 deficiency and/or that would benefit from increased mitochondrial activity in an infant human subject. In further embodiments, the invention relates to methods for promoting the growth of beneficial species of bacteria in the gut of an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6). In further embodiments, the invention relates to methods for promoting the gut health of an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6). In further embodiments, the invention relates to methods for reducing gastrointestinal inflammation in an infant human subject by administering to the infant human subject at least one compound selected from NR, NAR, and NMN, derivatives thereof, or salts thereof, alone or in combination with at least one of thiamine (vitamin B1), riboflavin (vitamin B2), niacin (vitamin B3), and pyridoxine (vitamin B6).

DETAILED DESCRIPTION

In one aspect, the present disclosure surprisingly demonstrates novel methods for delivering $NAD^+$-precursors to a human infant in need thereof. In a particular embodiment, methods for delivering at least one compound selected from nicotinamide riboside (NR), nicotinic acid riboside (NAR), and nicotinamide mononucleotide (NMN), derivatives thereof, or salts thereof, to an infant human subject in need of said compound or compounds are described. In another embodiment, the present disclosure relates to methods for delivering at least one compound selected from nicotinamide riboside (NR), nicotinic acid riboside (NAR), and nicotinamide mononucleotide (NMN), derivatives thereof, or salts thereof, in combination with at least one of thiamine (vitamin B1), riboflavin (vitamin B2), niacin (vitamin B3), and pyridoxine (vitamin B6) to an infant human subject in need of said compound or compounds. In yet another embodiment, the invention relates to methods for treating and/or preventing symptoms, diseases, disorders, or conditions associated with, or having etiologies involving, vitamin B3-deficiency and/or that would benefit from increased mitochondrial activity.

Nicotinamide riboside (NR) is a pyridinium nicotinyl compound having the formula (I):

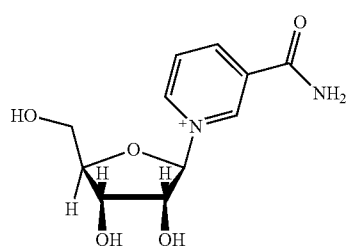

(I)

Nicotinic acid riboside (NAR) is a pyridinium nicotinyl compound having the formula (II):

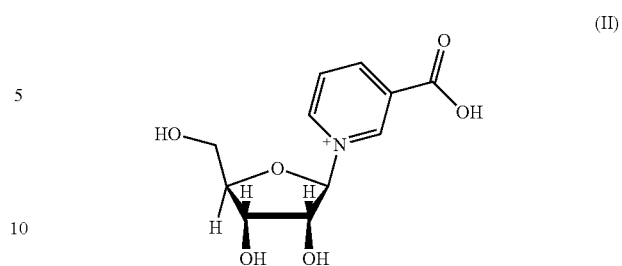

(II)

Nicotinamide mononucleotide (NMN) is a pyridinium nicotinyl compound having the formula (III):

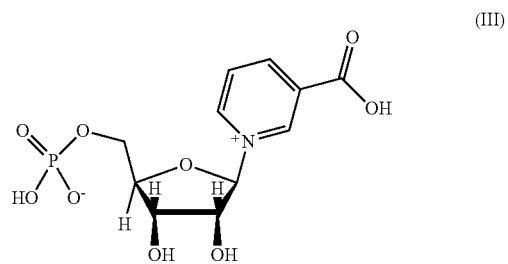

(III)

Reduced nicotinamide riboside ("NRH") is a 1,4-dihydropyridyl reduced nicotinyl compound having the formula (IV):

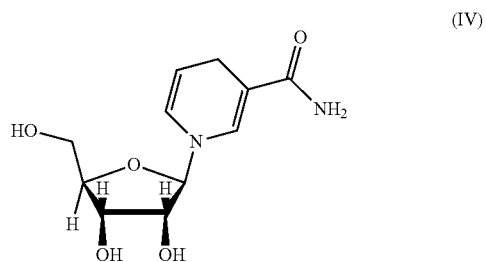

(IV)

Reduced nicotinic acid riboside ("NARH") is a 1,4-dihydropyridyl reduced nicotinyl compound having the formula (V):

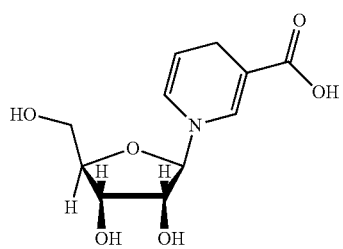

(V)

The free hydrogens of hydroxyl groups on the ribose moiety of nicotinamide riboside (NR, I) can be substituted with acetyl groups ($CH_3$—C(=O)—) to form 1-(2',3', 5'-triacetyl-beta-D-ribofuranosyl)-nicotinamide ("NR triacetate" or "NRTA") having the formula (VI):

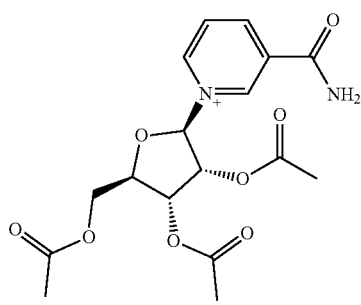

(VI)

The free hydrogens of hydroxyl groups on the ribose moiety of nicotinic acid riboside (NAR, II) can be substituted with acetyl groups (CH₃—C(=O)—) to form 1-(2',3',5'-triacetyl-beta-D-ribofuranosyl)-nicotinic acid ("NAR triacetate" or "NARTA") having the formula (VII):

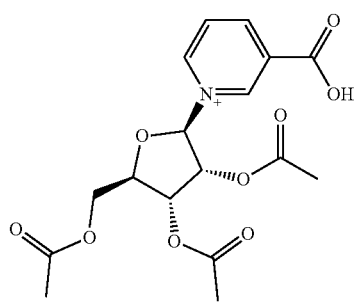

(VII)

The free hydrogens of hydroxyl groups on the ribose moiety of reduced nicotinamide riboside (NRH, IV) can be substituted with acetyl groups (CH₃—C(=O)—) to form 1-(2',3',5'-triacetyl-beta-D-ribofuranosyl)-1,4-dihydronicotinamide ("NRH triacetate" or "NRH-TA") having the formula (VIII):

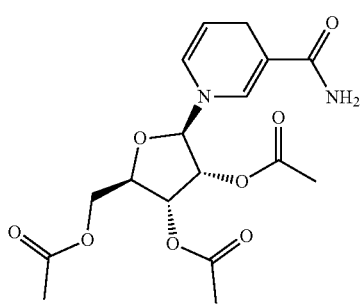

(VIII)

The free hydrogens of hydroxyl groups on the ribose moiety of reduced nicotinic acid riboside (NARH, V) can be substituted with acetyl groups (CH₃—C(=O)—) to form 1-(2',3',5'-triacetyl-beta-D-ribofuranosyl)-1,4-dihydronicotinic acid ("NARH triacetate" or "NARH-TA") having the formula (IX):

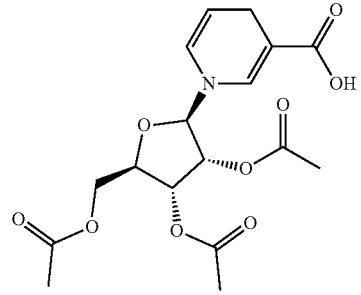

(IX)

Figure 1:
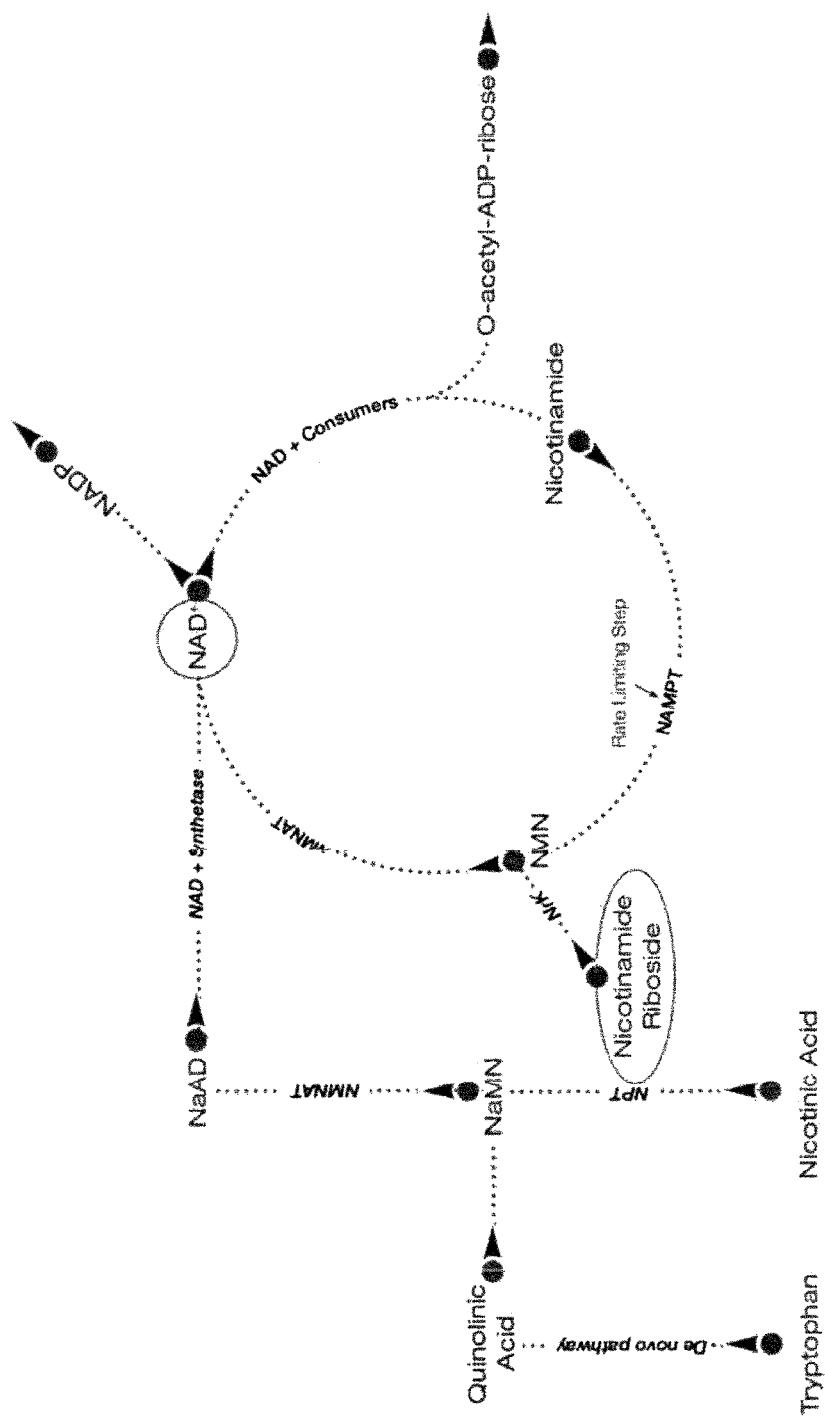
FIG. 1 depicts the $NAD^+$ biosynthetic pathway.

Without being bound by theory, it is believed that, as can be seen in the NAD⁺ biosynthetic pathway depicted in FIG. 1, nicotinamide riboside (NR, I) converts to nicotinamide mononucleotide (NMN, III) via phosphorylation by NR kinases (NRKs). Nicotinamide mononucleotide (NMN, III) is then converted to NAD⁺ by nicotinamide mononucleotide adenylyltransferase (NMNAT). Nicotinamide mononucleotide (NMN, III) is the only metabolite that can be converted to NAD⁺ in mitochondria, thus nicotinamide and nicotinamide riboside (NR, I) are the two candidate NAD⁺ precursors that can replenish NAD⁺ and improve mitochondrial fuel oxidation. However, nicotinamide riboside (NR, I) has a direct two step pathway to NAD⁺ synthesis that bypasses the rate-limiting step of the salvage pathway, conversion of nicotinamide to nicotinamide mononucleotide (NMN, III) via activity of nicotinamide phosphoribosyltransferase (NAMPT).

A healthy, growing infant requires a steady intake of essential nutrients, and a key component of that would be an NAD⁺ precursor. A human study examining NAD⁺ levels in human skin tissues demonstrated that the amount of NAD⁺ decreases with age. Thus, human infants have the highest concentration of NAD⁺ in their skin cells compared to older humans. Specifically, almost three times as much NAD⁺ is present in human newborns as compared to adults thirty to fifty years old. Further, human infants have approximately eight times as much NAD⁺ as compared to adults fifty-one to seventy years old. These results support the idea that human infants naturally need higher NAD⁺ levels during that stage of development.

Without being bound by theory, in a particular embodiment, it is believed that administering or delivering at least one compound selected from nicotinamide riboside (NR, I), nicotinic acid riboside (NAR, II), and nicotinamide mononucleotide (NMN, III), derivatives thereof, or salts thereof, would effectively provide higher levels of NAD⁺ to a human infant in need thereof than levels ordinarily received through human breast milk or presently commercially available infant formula products.

Without being bound by theory, in another particular embodiment, it is believed that administering or delivering at least one compound selected from nicotinamide riboside (NR, I), nicotinic acid riboside (NAR, II), and nicotinamide mononucleotide (NMN, III), derivatives thereof, or salts thereof, would treat and/or prevent symptoms, diseases, disorders, or conditions associated with, or having etiologies involving, vitamin B3 deficiency and/or that would benefit from increased mitochondrial activity.

Vitamin B3, which is also known as "nicotinic acid," or "niacin," is a pyridine compound having the formula (X):

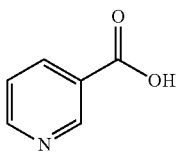

(X)

Without being bound by theory, it is believed that, as can be seen in the NAD⁺ biosynthetic pathway depicted in FIG. 1, vitamin B3 (nicotinic acid, or niacin, X) is converted via several intermediates to NAD⁺. Niacin is also known to include an admixture with nicotinamide (Nam or NM).

Vitamin B1, which is also known as thiamine, is a compound having the formula (XI):

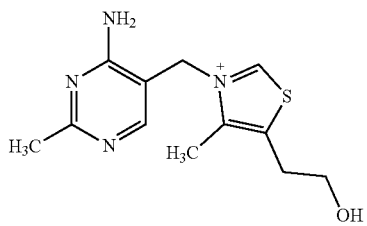

(XI)

Vitamin B2, which is also known as riboflavin, is a compound having the formula (XII):

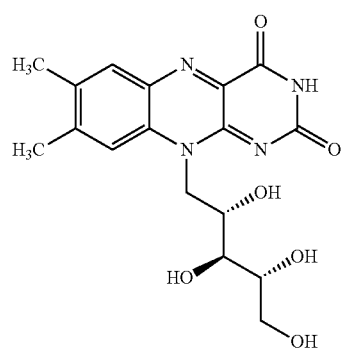

(XII)

Vitamin B6, which is also known as pyridoxine in the form most commonly given as a supplement, is a compound having the formula (XIII):

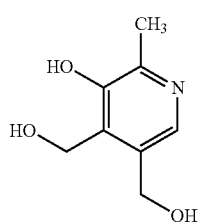

(XIII)

Without being bound by theory, vitamins B1, B2, B3, and B6 are believed to be closely intertwined in their biosynthetic pathways, with the maintenance and regeneration of the NAD(P)(H) intracellular pool depending on the availability of ThDP (B1), FAD (B2), and PLP (B6). Thiamine (vitamin B1, XI), riboflavin (vitamin B2, XII), and pyridoxine (vitamin B6, XIII) are salvaged from food and converted back intracellularly to their respective, bioactive forms: Thiamine (ThDP); Flavin Adenine Dinucleotide (FAD); Nicotinamide Adenine Dinucleotide (NAD⁺); and PyridoxaL Phosphate (PLP). The conversion of vitamins B1, B2, and B6 to ThDP, FAD, and PLP, respectively, is ATP-dependent. Two of the three salvage pathways that convert vitamin B3 to NAD⁺ are dependent on ThDP (B1), with the de novo production of NAD⁺ from tryptophan depending on the bioactive forms of vitamins B1, B2, and B6. The vitamin B1 dependency comes from the fact that ThDP (B1) is cofactor for the transketolases involved in the biosynthesis of phosphoriboside pyrophosphate, an essential substrate in these aforementioned NAD⁺ salvage and de novo pathways.

Without being bound by theory, in yet another embodiment, it is believed that at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, used alone or in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would effectively provide higher levels of NAD⁺ to a human infant in need thereof than levels ordinarily received through human breast milk or presently commercially available infant formula products, in a synergistic manner. It is expected that delivering at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, optionally in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would effectively provide higher levels of NAD⁺ to a human infant in need thereof than levels ordinarily received through human breast milk or presently commercially available infant formula products, and higher levels of NAD⁺ than either a nicotinyl compound (I, II, III, IV, V, VI, VII, VIII, and/or IX) or a vitamin (X, XI, XII, and/or XIII) alone.

Without being bound by theory, in yet another embodiment, it is believed that at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, used alone or in combination with one or more vitamins selected from vitamin B1 (thiamine, XI), vitamin B2, riboflavin, XII), vitamin B3 (nicotinic acid, or niacin, X), and vitamin B6 (pyridoxine in supplement form, XIII) would be used effectively to treat and/or prevent diseases, symptoms, disorders, or conditions associated with, or having etiologies involving, vitamin B3-deficiency or that would benefit from increased mitochondrial activity, in a human infant in need thereof, in a synergistic manner. It is expected that delivering at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would treat and/or prevent symptoms, diseases, disorders, or conditions associated with, or having etiologies involving, vitamin B3-deficiency or that would benefit from increased mitochondrial activity, in a human infant in need thereof more effectively than either a nicotinyl compound (I, II, III, IV, V, VI, VII, VIII, and/or IX) or a vitamin (X, XI, XII, and/or XIII) alone.

Without being bound by theory, in yet another embodiment, it is believed that at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, used alone or in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would effectively provide higher levels of beneficial species of bacteria in the gut of an infant human than levels ordinarily received through human breast milk or commercially available infant formula products, in a synergistic manner. It is expected that delivering at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, optionally in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would effectively provide higher levels of beneficial species of bacteria in the gut of an infant human than levels ordinarily received through human breast milk or presently commercially available infant formula products, and higher levels of beneficial species of bacteria in the gut of an infant human than either a nicotinyl compound (I, II, III, IV, V, VI, VII, VIII, and/or IX) or a vitamin (X, XI, XII, and/or XIII) alone.

Without being bound by theory, in yet another embodiment, it is believed that at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, used alone or in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would more effectively promote the gut health of an infant human subject than human breast milk or commercially available infant formula products, in a synergistic manner. It is expected that delivering at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, optionally in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would more effectively promote the gut health of an infant human subject than human breast milk or presently commercially available infant formula products, and more effectively promote the gut health of an infant human than either a nicotinyl compound (I, II, III, IV, V, VI, VII, VIII, and/or IX) or a vitamin (X, XI, XII, and/or XIII) alone.

Without being bound by theory, in yet another embodiment, it is believed that at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, used alone or in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would more effectively reduce gastrointestinal inflammation in an infant human subject than human breast milk or commercially available infant formula products, in a synergistic manner. It is expected that delivering at least one compound selected from nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), NR triacetate (NRTA, VI), NAR triacetate (NARTA, VII), NRH triacetate (NRH-TA, VIII), and NARH triacetate (NARH-TA, IX), or salts thereof, optionally in combination with one or more vitamins selected from vitamin B1 (thiamine, XI), vitamin B2 (riboflavin, XII), vitamin B3 (nicotinic acid, or niacin, X), and vitamin B6 (pyridoxine in supplement form, XIII) would more effectively reduce gastrointestinal inflammation in an infant human subject than human breast milk or presently commercially available infant formula products, and more effectively reduce gastrointestinal inflammation in an infant human than either a nicotinyl compound (I, II, III, IV, V, VI, VII, VIII, and/or IX) or a vitamin (X, XI, XII, and/or XIII) alone.

The embodiments of the present methods for delivering at least one nicotinyl compound (I, II, III, IV, V, VI, VII, VIII, and/or IX), or a salt thereof, alone or in combination with at least one vitamin (X, XI, XII, and/or XIII) to a human infant in need thereof described herein have not been demonstrated before.

Additionally, the embodiments of the present methods for delivery address limitations of existing technologies to deliver higher levels of NAD$^+$ to a human infant in need thereof than levels ordinarily received through human breast milk or presently commercially available infant formula products.

The embodiments of the present methods for treating and/or preventing symptoms, diseases, disorders, or conditions associated with, or having etiologies involving, vitamin B3 deficiency and/or that would benefit from increased mitochondrial activity in a human infant comprising administering or providing at least one nicotinyl compound (I, II, III, IV, V, VI, VII, VIII, and/or IX), or a salt thereof, alone or in combination with at least one vitamin (X, XI, XII, and/or XIII) described herein have not been demonstrated before.

Additionally, the embodiments of the present methods for treating and/or preventing symptoms, diseases, disorders, or conditions associated with, or having etiologies involving, vitamin B3 deficiency and/or that would benefit from increased mitochondrial activity in a human infant address limitations of existing technologies to treat or prevent symptoms, diseases, disorders, or conditions associated with, or having etiologies involving, vitamin B3 deficiency and/or that would benefit from increased mitochondrial activity.

In certain embodiments, the present disclosure provides methods for treating and/or preventing symptoms, diseases, disorders, or conditions associated with, or having etiologies involving, vitamin B3 deficiency. Exemplary symptoms, diseases, disorders, or conditions associated with, or having etiologies involving, vitamin B3 deficiency that may be treated and/or prevented in accordance with the methods described include indigestion, fatigue, canker sores, vomiting, poor circulation, burning in the mouth, swollen red tongue, and depression. Severe vitamin B3 deficiency can cause a condition known as pellagra, a premature aging condition that is characterized by cracked, scaly skin, dementia, and diarrhea. Other conditions characterized by premature or accelerated aging include Cockayne Syndrome, Neill-Dingwall Syndrome, progeria, and the like.

In certain embodiments, the present disclosure provides methods for treating and/or preventing symptoms, diseases, disorders, or conditions that would benefit from increased mitochondrial activity. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, symptoms, diseases, disorders, or conditions that would benefit from increased mitochondrial activity include symptoms, diseases, disorders, or conditions associated with mitochondrial dysfunction.

In certain embodiments, methods for treating and/or preventing symptoms, diseases, disorders, or conditions that would benefit from increased mitochondrial activity may comprise identifying a subject suffering from a mitochondrial dysfunction. Methods for diagnosing a mitochondrial dysfunction that may involve molecular genetic, pathologic, and/or biochemical analysis are summarized in Bruce H. Cohen & Deborah R. Gold, *Mitochondrial cytopathy in adults: what we know sofar,* 68 CLEVELAND CLINIC J. MED. 625 (2001), incorporated by reference herein in its entirety. One method for diagnosing a mitochondrial dysfunction is the Thor-Byrneier scale. See, e.g., Cohen & Gold, 2001. See also S. Collins et al., *Respiratory Chain Encephalomyopathies: A Diagnostic Classification,* 36 EUROPEAN NEUROLOGY 260 (1996), incorporated by reference herein in its entirety.

Mitochondria are critical for the survival and proper function of almost all types of eukaryotic cells. Mitochondria in virtually any cell type can have congenital or acquired defects that affect their function. Thus, the clinically significant signs and symptoms of mitochondrial defects affecting respiratory chain function are heterogeneous and variable depending on the distribution of defective mitochondria among cells and the severity of their deficits, and upon physiological demands upon the affected cells. Nondividing tissues with high energy requirements, e.g., nervous tissue, skeletal muscle, and cardiac muscle are particularly susceptible to mitochondrial respiratory chain dysfunction, but any organ system can be affected.

Symptoms, diseases, disorders, and conditions associated with mitochondrial dysfunction include symptoms, diseases, disorders, and conditions in which deficits in mitochondrial respiratory chain activity contribute to the development of pathophysiology of such symptoms, diseases, disorders, or conditions in a mammal. This includes congenital genetic deficiencies in activity of one or more components of the mitochondrial respiratory chain, wherein such deficiencies are caused by a) elevated intracellular calcium; b) exposure of affected cells to nitric oxide; c) hypoxia or ischemia; d) microtubule-associated deficits in axonal transport of mitochondria; or e) expression of mitochondrial uncoupling proteins.

Symptoms, diseases, disorders, or conditions that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis. Exemplary symptoms, diseases, disorders, or conditions that would benefit from increased mitochondrial activity include, for example, AMDF (Ataxia, Myoclonus and Deafness), auto-immune disease, cancer, CIPO (Chronic Intestinal Pseudoobstruction with myopathy and Ophthalmoplegia), congenital muscular dystrophy, CPEO (Chronic Progessive External Ophthalmoplegia), DEAF (Maternally inherited DEAFness or aminoglycoside-induced DEAFness), DEMCHO (Dementia and Chorea), diabetes mellitus (Type I or Type II), DIDMOAD (Diabetes Insipidus, Diabetes Mellitus, Optic Atrophy, Deafness), DMDF (Diabetes Mellitus and Deafness), dystonia, Exercise Intolerance, ESOC (Epilepsy, Strokes, Optic atrophy, and Cognitive decline), FBSN (Familial Bilateral Striatal Necrosis), FICP (Fatal Infantile Cardiomyopathy Plus, a MELAS-associated cardiomyopathy), GER (Gastrointestinal Reflux), HD (Huntington's Disease), KSS (Kearns Sayre Syndrome), "later-onset" myopathy, LDYT (Leber's hereditary optic neuropathy and DYsTonia), Leigh's Syndrome, LHON (Leber Hereditary Optic Neuropathy), LIMM (Lethal Infantile Mitochondrial Myopathy), MDM (Myopathy and Diabetes Mellitus), MELAS (Mitochondrial Encephalomyopathy, Lactic Acidosis, and Stroke-like episodes), MEPR (Myoclonic Epilepsy and Psychomotor Regression), MERME (MERRF/MELAS overlap disease), MERRF (Myoclonic Epilepsy and Ragged Red Muscle Fibers), MHCM (Maternally Inherited Hypertrophic CardioMyopathy), MICM (Maternally Inherited CardioMyopathy), MILS (Maternally Inherited Leigh Syndrome), Mitochondrial Encephalocardiomyopathy, Mitochondrial Encephalomyopathy, MM (Mitochondrial Myopathy), MMC (Maternal Myopathy and Cardiomyopathy), MNGIE (Myopathy and external ophthalmoplegia, Neuropathy, Gastro-Intestinal, Encephalopathy), Multisystem Mitochondrial Disorder (myopathy, encephalopathy, blindness, hearing loss, peripheral neuropathy), NARP (Neurogenic muscle weakness, Ataxia, and Retinitis Pigmentosa; alternate phenotype at this locus is reported as Leigh Disease), Pearson's Syndrome, PEM (Progressive Encephalopathy), PEO (Progressive External Ophthalmoplegia), PME (Progressive Myoclonus Epilepsy), PMPS (Pearson Marrow-Pancreas Syndrome), psoriasis, RTT (Rett Syndrome), schizophrenia, SIDS (Sudden Infant Death Syndrome), SNHL (SensoriNeural Hearing Loss), Varied Familial Presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), or Wolfram syndrome.

Other symptoms, diseases, disorders, and conditions that would benefit from increased mitochondrial activity include, for example, Friedreich's ataxia and other ataxias, amyotrophic lateral sclerosis (ALS) and other motor neuron diseases, macular degeneration, epilepsy, Alpers syndrome, Multiple mitochondrial DNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, Refractory epilepsy with declines during infection, Autism with declines during infection, Cerebral palsy with declines during infection, maternally inherited thrombocytopenia and leukemia syndrome, MARIAHS syndrome (Mitochondrial Ataxia, Recurrent Infections, Aphasia, Hypouricemia/hypomyelination, Seizures, and dicarboxylic aciduria), ND6 dystonia, Cyclic vomiting syndrome with declines during infection, 3-Hydroxy isobutyric aciduria with lactic acidemia, Diabetes mellitus with lactic acidemia, Uridine Responsive Neurologic Syndrome (URNS), Dilated cardiomyopathy, Splenic Lymphoma, or Renal Tubular Acidosis/Diabetes/Ataxissyndrome.

In other embodiments, the present disclosure provides methods for treating a human infant suffering from mitochondrial disorders arising from, but not limited to, Post-traumatic head injury and cerebral edema, Stroke (invention methods useful for treating or preventing reperfusion injury), Lewy body dementia, Hepatorenal syndrome, Acute liver failure, NASH (Non-Alcoholic SteatoHepatitis), Antimetastasis/prodifferentiation therapy of cancer, Idiopathic congestive heart failure, Atrial fibrillation (non-valvular), Wolff-Parkinson-White Syndrome, Idiopathic heart block, Prevention of reperfusion injury in acute myocardial infarctions, Familial migraines, Irritable bowel syndrome, Secondary prevention of non-Q wave myocardial infarctions, Premenstrual syndrome, Prevention of renal failure in hepatorenal syndrome, Anti-phospholipid antibody syndrome, Eclampsia/pre-eclampsia, Ischemic heart disease/Angina, and Shy-Drager and unclassified dysautonomia syndromes.

Common symptoms of mitochondrial diseases include cardiomyopathy, muscle weakness and atrophy, developmental delays (involving motor, language, cognitive, or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, hepatic failure, lactic acidemia, and diabetes mellitus.

In exemplary embodiments, the present disclosure provides methods for treating diseases or disorders that would benefit from increased mitochondrial activity by administering to a human infant a therapeutically effective amount of at least one nicotinyl compound (I, II, III, IV, V, VI, VII, VIII, and/or IX), or a salt thereof, alone or in combination with at least one vitamin (X, XI, XII, and/or XIII). Exemplary diseases or disorders include, but are not limited to, for example, neuromuscular disorders (e.g., Friedreich's Ataxia, muscular dystrophy, multiple sclerosis, etc.), disorders of neuronal instability (e.g., seizure disorders, migraine, etc.), developmental delay, ischemia, renal tubular acidosis, chemotherapy fatigue, mitochondrial myopathies, mitochondrial damage (e.g., calcium accumulation, excitotoxicity, nitric oxide exposure, hypoxia, etc.), and mitochondrial deregulation.

A gene defect underlying Friedreich's Ataxia (FA), the most common hereditary ataxia, was recently identified and is designated "frataxin." In FA, after a period of normal development, deficits in coordination develop that progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes. The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction. When intermediate numbers of GAA repeats are present in the frataxin gene intron, the severe clinical phenotype of ataxia may not develop. However, these intermediate-length trinucleotide extensions are found in 25 to 30% of patients with non-insulin dependent diabetes mellitus, compared to about 5% of the nondiabetic population. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be used for treating human infants with disorders related to deficiencies or defects in frataxin, including Friedreich's Ataxia, myocardial dysfunction, diabetes mellitus, and complications of diabetes-like neuropathy.

Muscular dystrophy refers to a family of diseases involving deterioration of neuromuscular structure and function, often resulting in atrophy of skeletal muscle and myocardial dysfunction. In the case of Duchenne muscular dystrophy, mutuations, or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration, in most cases, is calcium-mediated impairment of mitochondrial function. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be used for reducing the rate of decline in muscular functional capacities and for improving muscular functional status in human infants with muscular dystrophy.

Epilepsy is often present in patients with mitochondrial cytopathies, involving a range of seizure severity and frequency, e.g., absence, tonic, atonic, myoclonic, and status epilepticus, occurring in isolated episodes or many times daily. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be used for treating human infants with seizures secondary to mitochondrial dysfunction, including reducing frequency and severity of seizure activity.

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved in activation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like excitotoxic or nitric oxide-mediated mitochondrial dysfunction) or other conditions resulting in impaired pyrimidine synthesis, cell proliferation and axonal extension are impaired at crucial stages in development of neuronal interconnections and circuits, resulting in delayed or arrested development of neuropsychological functions like language, motor, social, executive function, and cognitive skills. In autism, for example, magnetic resonance spectroscopy measurements of cerebral phosphate compounds indicate that there is global undersynthesis of membranes and membrane precursors indicated by reduced levels of uridine diphosphosugars, and cytidine nucleotide derivatives involved in membrane synthesis. Disorders characterized by developmental delay include Rett's Syndrome, pervasive developmental delay (or PDD-NOS "pervasive developmental delay not otherwise specified" to distinguish it from specific subcategories like autism), autism, Asperger's Syndrome, and Attention Deficit/Hyperactivity Disorder (ADHD), which is becoming recognized as a delay or lag in development of neural circuitry underlying executive functions. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII), may be useful for treating human infants with neurodevelopmental delays (e.g., involving motor, language, executive function, and cognitive skills), or other delays or arrests of neurological and neuropsychological development in the nervous system and somatic development in non-neural tissues like muscle and endocrine glands.

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation. In conditions like cerebral anoxia, angina, or sickle cell anemia crises, tissues are relatively hypoxic. In such cases, compounds that increase mitochondrial activity provide protection of affected tissues from deleterious effects of hypoxia, attenuate secondary delayed cell death, and accelerate recovery from hypoxic tissue stress and injury. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treating and/or preventing delayed cell death (apoptosis in regions like the hippocampus or cortex occurring about 2 to 5 days after an episode of cerebral ischemia) after ischemic or hypoxic insult to the brain.

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treating and/or preventing renal tubular acidosis and other forms of renal dysfunction caused by mitochondrial respiratory chain deficits.

Mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue," prolonged periods of weakness and exercise intolerance that may persist even after recovery from hematologic and gastrointestinal toxicities of such agents. In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treatment and/or prevention of side effects of cancer chemotherapy related to mitochondrial dysfunction.

In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treatment and/or prevention of mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limbgirdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendlian inheritance pattern. Mutations in nuclear-encoded mitochondrial enzymes occur.

In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treating patients suffering from toxic damage to mitochondria, such as toxic damage due to calcium accumulation, excitotoxicity, nitric oxide exposure, drug induced toxic damage, or hypoxia.

A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, because calcium uptake into mitochondria results in diminished capabilities for energy transduction.

Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide (about 1 micromolar) inhibits cytochrome oxidase (Complex IV) and thereby inhibits mitochondrial respiration; moreover, prolonged exposure to nitric oxide (NO) irreversibly reduces Complex I activity. Physiological or pathophysiological concentrations of NO thereby inhibit pyrimidine biosynthesis. Nitric oxide is implicated in a variety of neurodegenerative disorders including inflammatory and autoimmune diseases of the central nervous system, and is involved in mediation of excitotoxic and post-hypoxic damage to neurons.

Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

In certain embodiments, a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for treating and/or preventing diseases or disorders associated with mitochondrial deregulation.

Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol that affect microtubule stability, mitochondria distant from the nucleus undergo loss of cytochrome oxidase activity. Accordingly, in certain embodiments, treatment with a therapeutically effective amount of at least one nicotinyl compound (I, II, III, IV, V, VI, VII, VIII, and/or IX), or salt thereof, alone or in combination with at least one vitamin (X, XI, XII, and/or XIII) may be useful for promoting nuclear-mitochondrial interactions.

Mitochondria are the primary source of free radicals and reactive oxygen species, due to spillover from the mitochondrial respiratory chain, especially when defects in one or more respiratory chain components impairs orderly transfer of electrons from metabolic intermediates to molecular oxygen. To reduce oxidative damage, cells can compensate by expressing mitochondrial uncoupling proteins ("UCPs"), of which several have been identified. UCP-2 is transcribed in response to oxidative damage, inflammatory cytokines, or excess lipid loads, e.g., fatty liver and steatohepatitis. UCPs reducer spillover of reactive oxygen species from mitochondria by discharging proton gradients across the mitochondrial inner membrane, in effect wasting energy produced by metabolism and rendering cells vulnerable to energy stress as a trade-off for reduced oxidative injury.

In certain embodiments, the present disclosure provides a method of protecting a human infant from chronic inflammation that can cause abnormal neurogenesis. Formula-fed infants can be dysbiotic, meaning that their gut microflora are not the same as they would be if such infants were breast-fed. For example, Bifdobacteria is more prevalent in the gut of breast-fed infants as compared to formula-fed infants. See Gordon Cooke et al., *Comparing the gut flora of Irish breastfed and formula-fed neonates aged between birth and 6 weeks old,* 17 MICROBIAL ECOLOGY IN HEALTH & DISEASE 163 (2005), incorporated by reference herein in its entirety. Further, *E. coli* and Enterococci, were more prevalent in the gut of infants fed formula. This observed dysbiosis can produce endotoxins that promote inflammation, and that in turn can inhibit neurogenesis. Raz Yirmiya & Inbal Goshen, *Immune modulation of learning, memory, neural plasticity, and neurogenesis,* 25 BRAIN, BEHAVIOR, & IMMUNITY 181 (2011), incorporated by reference herein in its entirety. Further, nicotinamide (Nam or NM) has been shown to lower inflammation and cognitive impairment in rats. See Ying Wang & Min Zuo, *Nicotinamide improves sevoflurane-induced cognitive impairment through suppression of inflammation and anti-apoptosis in rat,* 8 INT'L J. CLIN. EXP. MED. 20079 (2015), incorporated by reference herein in its entirety. It is believed that certain embodiments of the present invention will suppress inflammation and promote healthy neurogenesis. It is further believed that certain embodiments of the present disclosure will promote a healthy gut-brain axis that is instrumental to healthy brain development and function.

In another embodiment, the present disclosure provides a method for meeting the optimizing the protein energy needs of a preterm infant to promote healthy neurological development. These preterm infants are at high risk of malnutrition. There is a well-established link between energy metabolism and neurodevelopment. See Kristin Keunen et al., *Impact of nutrition on brain development and its neuroprotective implications following preterm birth,* 77 PEDIATRIC RESEARCH 148 (2015), incorporated by reference herein in its entirety. Normally, in late-term gestation, important brain growth and brain maturation takes place. Certain embodiments of the present disclosure provide a method for healthy neurogenesis in premature infants as well as in full term infants. First week protein and energy intake has been shown to be especially beneficial for premature, very low-weight babies. Bonnie E. Stephens et al., *First-Week Protein and Energy Intakes Are Associated With 18-Month Developmental Outcomes in Extremely Low Birth Weight Infants,* 123 PEDIATRICS 1337 (2009), incorporated by reference herein in its entirety. It has been shown that nicotinamide riboside (NR, I) is an efficient NAD$^+$ precursor, and thus should be administered to any infant whose energy demand is critical.

In another embodiment, the present disclosure provides a method of treating a human infant in need of preventing and/or reversing early obesogenic programming. Studies have shown that an obesogenic maternal diet can affect fetal growth, which can lead to health implications later in life. Amanda N. Sferruzzi-Perri et al., *An obesogenic diet during mouse pregnancy modifies maternal nutrient partitioning and the fetal growth trajectory,* FASEB J. 3928 (2013), incorporated by reference herein in its entirety. Nicotinamide riboside (NR, I) has been shown to more efficiently metabolize a high-fat diet, and thus it is believed that nicotinamide riboside (NR, I) will have anti-obesogenic effects. Specifically, mice on a high-fat diet have been shown to gain 40% less weight when supplemented with nicotinamide riboside (NR, I). Carles Cantó et al., *The NAD$^+$ Precursor Nicotinamide Riboside Enhances Oxidative Metabolism and Protects Against High-Fat Diet-Induced Obesity,* 15 CELL METABOLISM 838 (2012), incorporated by reference herein in its entirety.

In another embodiment, the present disclosure provides a method for supplementing infant formula with an important vitamin required in early infant development. One study documenting the vitamin B content of human breast milk over time demonstrated, surprisingly, that B vitamins are lower in the colostrums than in mature milk. See Xiangnan Ren et al., *B-Vitamin Levels in Human Milk among Different Lactation Stages and Areas in China*, 10 PLoS ONE e0133285 (2015), incorporated by reference herein in its entirety. Ren et al. only looked at niacin (X) and nicotinamide (Nam or NM) for vitamin B3 content. It is believed that nicotinamide riboside (NR, I) is the important vitamin B3 source in early milk production, essential for the energy demand of a rapidly developing infant.

Salts of Nicotinyl Compounds (I, II, III, IV, V, VI, VII, VIII, and IX) According to the Present Invention The methods of using nicotinyl compounds (I, II, III, IV, V, VI, VII, VIII, and IX) of the present invention may take the form of salts. The term "salts" embraces addition salts of free acids or free bases that are nicotinyl compounds (I, II, III, IV, V, VI, VII, VIII, and IX) of the methods of the present invention. The term "pharmaceutically acceptable salt" refers to salts that possess toxicity profiles within a range that affords utility in pharmaceutical applications.

Suitable pharmaceutically acceptable acid addition salts may be prepared from an inorganic acid or from an organic acid. Examples of organic acids include hydrochloric, hydrobromic, hydroiodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, O-hydroxybutyric, salicylic, galactaric, and galacturonic acid. In the present examples of uses of nicotinyl compounds (I, II, III, IV, V, VI, VII, VIII, and IX), i.e., compounds containing amino groups and pyridinium groups, said compounds can be isolated as salts of inorganic acids or strong organic acids, e.g., hydrochloric acid or trifluoroacetic acid.

Suitable pharmaceutically acceptable base addition salts of nicotinyl compounds of the methods of the invention include, but are not limited to, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl)aminomethane), and procaine.

Optionally wherein a basic counterion, or anion, is present, said basic counterion or anion is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, and trifluoroacetate; and, optionally the basic counterion, or anion, is an internal salt;

optionally the basic counterion, or anion, is an anion of a substituted or unsubstituted carboxylic acid selected from a monocarboxylic acid, a dicarboxylic acid, or a polycarboxylic acid;

optionally the basic counterion, or anion, is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and, optionally the basic counterion, or anion, is an anion of an unsubstituted monocarboxylic acid selected from formic acid, acetic acid, propionic acid, or butyric acid, the anions being formate, acetate, propionate, and butyrate, respectively; and, optionally the basic counterion, or anion, is an anion of a substituted or unsubstituted amino acid, i.e. amino-monocarboxylic acid or an amino-dicarboxylic acid, optionally selected from glutamic acid and aspartic acid, the anions being glutamate and aspartate, respectively; and, optionally the basic counterion, or anion, is an anion of ascorbic acid, being ascorbate; and, optionally the basic counterion, or anion, is a halide selected from fluoride, chloride, bromide, or iodide; and, optionally the basic counterion, or anion, is an anion of a substituted or unsubstituted sulfonate, further optionally a trihalomethanesulfoante selected from trifluoromethanesulfonate, tribromomethanesulfonate, or trichloromethanesulfonate; and, optionally the basic counterion, or anion, is an anion of a substituted or unsubstituted carbonate, further optionally hydrogen carbonate.

All of these salts may be prepared by conventional means from the corresponding nicotinyl compounds (I, II, III, IV, V, VI, VII, VIII, and IX) by reacting, for example, the appropriate acid or base with the nicotinyl compounds (I, II, III, IV, V, VI, VII, VIII, and IX). Preferably, the salts are in crystalline form, or alternatively in dried or freeze-dried form. The person skilled in the art will know how to prepare and select suitable forms, for example, as described in P. H. STAHL & C. G. WERMUTH, HANDBOOK OF PHARMACEUTICAL SALTS: PROPERTIES, SELECTION, AND USE (Wiley-VCH 2012), incorporated by reference herein in its entirety.

Delivery and Administration Systems of the Present Invention

The methods described herein may comprise administering daily, or every other day, or once a week, a high dose of one or more nicotinyl compound (I, II, III, IV, V, VI, VII, VIII, and/or IX), or salt thereof, alone or in combination with one or more vitamin (X, XI, XII, and/or XIII), e.g., in the form of a pill, to a subject. In embodiments where the high dose of one or more nicotinyl compound (I, II, III, IV, V, VI, VII, VIII, and/or IX), or salt thereof, alone or in combination with one or more vitamin (X, XI, XII, and/or XIII), is administered daily to the subject, the one or more nicotinyl compound (I, II, III, IV, V, VI, VII, VIII, and/or IX), or salt thereof, alone or in combination with one or more vitamin (X, XI, XII, and/or XIII), may be administered once a day. In other embodiments, it is administered twice or three times a day.

In some embodiments, the high dose of one or more nicotinyl compound (I, II, III, IV, V, VI, VII, VIII, and/or IX), or salt thereof, alone or in combination with one or more vitamin (X, XI, XII, and/or XIII), is administered in a sustained release formulation, e.g., by embedding or encapsulating the one or more nicotinyl compound (I, II, III, IV, V, VI, VII, VIII, and/or IX), or salt thereof, alone or in combination with one or more vitamin (X, XI, XII, and/or XIII), into neoparticles for delivery over a period of at least 12 hours, to a subject. In embodiments where the one or more nicotinyl compound (I, II, III, IV, V, VI, VII, VIII, and/or IX), or salt thereof, alone or in combination with one or more vitamin (X, XI, XII, and/or XIII), is administered to a subject in a sustained release formulation, a high dose of the one or more nicotinyl compound (I, II, III, IV, V, VI, VII, VIII, and/or IX), or salt thereof, alone or in combination with one or more vitamin (X, XI, XII, and/or XIII), may be administered for sustained delivery over a period of, for example, at least about 12, 15, 18, 24, or 36 hours, or longer. In other embodiments, it is administered for a sustained delivery over a period of one or more days. In yet other embodiments, it is administered for a sustained delivery over a period of one or more weeks.

In certain embodiments, the one or more nicotinyl compound (I, II, III, IV, V, VI, VII, VIII, and/or IX), or salt thereof, alone or in combination with one or more vitamin (X, XI, XII, and/or XIII), are administered in a nutraceutical formulation. A "nutraceutical" is any functional food (including beverages) that provides an additional benefit other than its nutritional benefit. In a preferred embodiment, a nutraceutical is provided and contains from about 0.1% to about 99%, or from about 0.1% to about 10%, of one or more nicotinyl compound (I, II, III, IV, V, VI, VII, VIII, and/or IX), or salt thereof, alone or in combination with one or more vitamin (X, XI, XII, and/or XIII), by weight. In preferred embodiments, a high dose as described herein of one or more nicotinyl compound (I, II, III, IV, V, VI, VII, VIII, and/or IX), or salt thereof, alone or combination with one or more vitamin (X, XI, XII, and/or XIII), is administered in a single serving of a food or beverage. In a preferred formulation, a single dosage form is provided (e.g., an 8 fluid ounce serving of a beverage such as water, flavored water, or fruit juice) that contains a quantity of one or more nicotinyl compound (I, II, III, IV, V, VI, VII, VIII, and/or IX), or salt thereof, alone or in combination with one or more vitamin (X, XI, XII, and/or XIII), that has a physiological effect equal to or greater than the physiological effect of 25 mg total of one or more nicotinyl compound (I, II, III, IV, V, VI, VII, VIII, and/or IX), or salt thereof, alone or in combination with one or more vitamin (X, XI, XII, and/or XIII). In other embodiments, a single dosage form is provided that contains a quantity of total one or more nicotinyl compound (I, II, III, IV, V, VI, VII, VIII, and/or IX), or salt thereof, alone or in combination with one or more vitamin (X, XI, XII, and/or XIII), that has a physiological effect equal to or greater than the physiological effect of about 10, 15, 20, 25, 50, 60, 75, 80, 100, 150, 200, or more mg one or more nicotinyl compound (I, II, III, IV, V, VI, VII, VIII, and/or IX), or salt thereof, alone or in combination with one or more vitamin (X, XI, XII, and/or XIII), per 8 fluid ounces. In other preferred embodiments, a single dosage form is provided (e.g., a serving of food such as a nutrition bar) that contains a total quantity of one or more nicotinyl compound (I, II, III, IV, V, VI, VII, VIII, and/or IX), or salt thereof, alone or in combination with one or more vitamin (X, XI, XII, and/or XIII), that has a physiological effect equal to or greater than the physiological effect of 100 mg one or more nicotinyl compound (I, II, III, IV, V, VI, VII, VIII, and/or IX), or salt thereof, alone or in combination with one or more vitamin (X, XI, XII, and/or XIII). In some embodiments, the food supplies 100 to 500 kcal per serving. In other embodiments, a single dosage form is provided that contains a total quantity of one or more nicotinyl compound (I, II, III, IV, V, VI, VII, VIII, and/or IX), or salt thereof, alone or in combination with one or more vitamin (X, XI, XII, and/or XIII), that has a physiological effect equal to or greater than the physiological effect of 20, 50, 60, 75, 80, 100, 150, 200, 250, or more, mg one or more nicotinyl compound (I, II, III, IV, V, VI, VII, VIII, and/or IX), or salt thereof, alone or in combination with one or more vitamin (X, XI, XII, and/or XIII), per 100 to 500 kcal. The phrase "total quantity of one or more nicotinyl compound (I, II, III, IV, V, VI, VII, VIII, and/or IX), or salt thereof, alone or in combination with one or more vitamin (X, XI, XII, and/or XIII)" refers to the total amount of one or more nicotinyl compound (I, II, III, IV, V, VI, VII, VIII, and/or IX), or salt thereof, alone or in combination with one or more vitamin (X, XI, XII, and/or XIII), present in the single dosage form.

In various embodiments, a nutraceutical comprising one or more nicotinyl compound (I, II, III, IV, V, VI, VII, VIII, and/or IX), or salt thereof, alone or in combination with one or more vitamin (X, XI, XII, and/or XIII), may be any variety of food or drink. For example, nutraceuticals may include drinks such as nutritional drinks, diet drinks (e.g., Slimfast™, Boost™, and the like) as well as sports, herbal, and other fortified beverages. Additionally, nutraceuticals may include food intended for human or animal consumption such as baked goods, for example, bread, wafers, cookies, crackers, pretzels, pizza, and rolls; ready-to-eat ("RTE") breakfast cereals, hot cereals; pasta products; snacks such as fruit snacks, salty snacks, grain snacks, nutrition bars, and microwave popcorn; dairy products such as yogurt, cheese, and ice cream; sweet goods such as hard candy, soft candy, and chocolate; beverages; animal feed; pet foods such as dog food and cat food; aqua-culture foods such as fish food and shrimp feed; and special purpose foods such as baby food, infant formulas, hospital food, medical food, sports food, performance food, or nutritional bars; fortified foods; food preblends; or mixes for home or food service use, such as preblends for soups or gravy, dessert mixes, dinner mixes, baking mixes such as bread mixes and cake mixes, and baking flower. In certain embodiments, the food or beverage does not include one or more of grapes, mulberries, blueberries, raspberries, peanuts, milk, yeast, or extracts thereof.

In certain embodiments, methods for delivering the one or more nicotinyl compound (I, II, III, IV, V, VI, VII, VIII, and/or IX), or salt thereof, alone or in combination with one or more vitamin (X, XI, XII, and/or XIII), of the present invention to a human infant in need thereof, and methods of treating and/or preventing symptoms, diseases, disorders, or conditions associated with, or having etiologies involving, vitamin B3 deficiency and/or that would benefit from increased mitochondrial activity in a human infant comprise delivering or administering an infant formula.

In certain embodiments, the one or more nicotinyl compound (I, II, III, IV, V, VI, VII, VIII, and/or IX), or salt thereof, alone or in combination with one or more vitamin (X, XI, XII, and/or XIII) are delivered by being "encased," "encapsulated," and/or "microencapsulated" in alginate. This method of delivery is currently used in infant formulas for babies with bad reflux. This alginate method of delivery allows for a slow release mechanism for nicotinyl compound delivery by mouth, and could be used for babies with bad reflux and/or as a method of stabilizing nicotinyl compound in any liquid including infant formula. Microencapsulation techniques are well known in the art.

Nutritional components of infant formulas are known in the art and one with knowledge in the art would be able to adjust formula compositions to include nicotinyl compound (I, II, III, IV, V, VI, VII, VIII, and/or IX), or salt thereof, alone or in combination with one or more vitamin (X, XI, XII, and/or XIII). For example, an infant formula typically contains a protein component comprising from about 6% to about 25% of the total caloric content of the infant formula; a carbohydrate component comprising from about 35% to about 50% of the total caloric content of the infant formula; and a lipid component comprising from about 30% to about 50% of the total caloric content of the infant formula. These ranges are provided as examples only, and are not intended to be limiting.

In infant formula, tryptophan becomes the first limiting amino acid when the protein content is reduced and no free amino acids are added. See Manja Fledderman et al., *Energetic Efficiency of Infant Formulae: A Review*, 64 ANNALS OF NUTRITION & METABOLISM 276 (2014), incorporated by reference herein in its entirety. One essential function of tryptophan is as an $NAD^+$ precursor. It is expected that addition of nicotinamide riboside (NR, I), nicotinic acid riboside (NAR, II), nicotinamide mononucleotide (NMN, III), reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and/or reduced nicotinic acid riboside triacetate (NARH-TA, IX), or salt thereof, alone or in combination with one or more vitamin (X, XI, XII, and/or XIII), to infant formula will release tryptophan from being consumed for $NAD^+$ synthesis, as all nine of these nicotinyl compounds are more efficient $NAD^+$ precursors. Thus, it is expected that it will take a longer period of time before tryptophan becomes limiting.

Examples of suitable fat sources typically include high oleic safflower oil, soy oil, fractionated coconut oil (medium chain triglycerides, MCT oil), high oleic sunflower oil, corn oil, canola oil, coconut, palm, and palm kernel oils, marine oil, cottonseed oil, walnut oil, wheat germ oil, sesame oil, cod liver oil, and peanut oil. Any single fat listed above, or any combination thereof, as appropriate, may be utilized. Other suitable fats will be readily apparent to those skilled in the art.

Additional components of infant formula typically include, for example, protein, carbohydrates, and minerals. Examples of suitable protein sources for an infant typically include casein, whey, condensed skim milk, nonfat milk, soy, pea, rice, wheat, corn, hydrolyzed protein, free amino acids, and protein sources that contain calcium in a colloidal suspension with the protein. Any single protein listed above, or any combination thereof, as appropriate, may be utilized. Other suitable proteins will be readily apparent to those skilled in the art.

A third component of infant formula is a source of carbohydrates. Carbohydrates are a major source of readily available energy that the infant needs for growth and that protects the infant from tissue catabolism. In human milk and most standard milk-based infant formulas, the carbohydrate is lactose. The carbohydrates that may be used in the infant formula can vary widely. Examples of carbohydrates suitable for infants typically include cereal grains, hydrolyzed cornstarch, maltodextrin, glucose polymers, sucrose, lactose, corn syrup, corn syrup solids, rice syrup, glucose, fructose, high fructose corn syrup, and indigestible oligosaccharides such as fructooligosaccharides ("FOS"). Any single carbohydrate listed above, or any combination thereof, as appropriate, may be utilized. Other suitable carbohydrates will be readily apparent to those skilled in the art.

An infant formula typically includes supplemented vitamins and minerals. Examples of minerals that may be added to infant formula typically include calcium, phosphorus, magnesium, zinc, manganese, copper, sodium, potassium, chloride, iron, and selenium. The additional nutrients chromium, molybdenum, iodine, taurine, carnitine, and choline may also be included.

In a certain embodiment, an exemplary composition for an infant formula for this invention, which adheres to the Food & Drug Administration's regulation codified at 21 C.F.R. § 107.100, pertaining to infant formula, is as follows for each 100 kilocalories (kcal): protein in a range of about 1.8 g-4.5 g, which can be selected from whey protein and/or casein; fat in the range of about 30%-54% of the total calories can be selected from palm oil and/or soy oil; linoleic acid, at a minimum of about 2.7% of total calories, which can be supplement with docosahexaeonic acid ("DHA") and arachidonic acid ("ARA"); and other vitamins and/or minerals, which will be added according to 21 C.F.R. § 107.100 guidelines, the only deviation from those guidelines of which will be the amount of B vitamins (X, XI, XII, and/or XIII) added to the formula. Niacin (X) levels will be added at minimum recommended levels, while the amounts of Vitamin B1 (XI), Vitamin B2 (XII), and/or Vitamin B6 (XIII) will all be increased proportionally with the amount of nicotinamide riboside (NR, I) added, because these vitamins support the metabolism of nicotinamide riboside (NR, I). Thus, for every 300 µg nicotinamide riboside (NR, I) added per 100 kilocalories, about 40 µg Vitamin B1 (XI), about 60 µg Vitamin B2 (XII), and about 35 µg Vitamin B6 (XIII) will be added, respectively. Ranges of about 100 µg to about 600 µg nicotinamide riboside (NR, I) are preferred per 100 kilocalories (kcal).

In other embodiments, ranges of nicotinamide riboside (NR, I) of about 1 µg to about 10,000 µg per 100 kilocalories (kcal) of infant formula.

In alternative embodiments, at least one of nicotinyl compounds II, III, IV, V, VI, VII, VIII, and/or IX may be used in similar ranges optionally in combination with nicotinamide riboside (NR, I).

Infant formulas may be prepared as any product form suitable for use in infants, including reconstitutable powders, ready-to-feed liquids, and dilutable liquid concentrates, which product forms are all well known in the nutritional formula art. As used in the present application, the amounts of components present in infant formula compositions refer to the amounts when the formula is ready for consumption by the infant. It is to be understood that in the case of a reconstitutable powder or dilutable liquid concentrate, the component amounts will be adjusted such that when the infant formula composition is reconstituted or diluted the amounts are as described herein. Thus, for example, reference to an infant formula composition that is to be diluted by, for example, addition of one part water for one part infant formula, wherein the infant formula composition has a given component concentration, when ready for consumption, is intended to cover an infant formula composition having a concentration of the component of twice the given amount, before it is made ready for consumption by the addition of water. Methods to prepare infant formulas are known to those skilled in the art. For example, the one or more nicotinyl compound (I, II, III, IV, V, VI, VII, VIII, and/or IX), or salt thereof, alone or in combination with one or more vitamin (X, XI, XII, and/or XIII), can be added directly to a liquid formula composition at a suitable point in the manufacturing process.

Infant formula can optionally be sterilized and subsequently used on a ready-to-feed basis, or can be stored as a concentrate. The concentrate can be prepared by spray drying the liquid formula prepared as above, and the formula can be reconstituted by rehydrating the concentrate. The infant formula concentrate is a stable liquid and has a suitable shelf life.

The one or more nicotinyl compound (I, II, III, IV, V, VI, VII, VIII, and/or IX), or salt thereof, alone or in combination with one or more vitamin (X, XI, XII, and/or XIII), used in the methods of the present invention can be microencapsulated prior to the addition into a formula composition. The choice of coating for the microencapsulation is determined by its lack of toxicity, desired particle size, and stability under the processing conditions for instant formulas, particularly sterilization. Any conventionally acceptable substantially oxygen-impermeable coating can be used. Such conventional microencapsulating methods and coating materials are well within the purview of one skilled in the art, and the specific microencapsulating method and coating are not peculiar to the present invention.

In certain embodiments, nicotinamide riboside (NR, I) binding of whey and/or protein can also be used to stabilize nicotinamide riboside (NR, I) in a liquid formulation.

For powder embodiments of infant formulas comprising one or more nicotinyl compound (I, II, III, IV, V, VI, VII, VIII, and/or IX), or salt thereof, alone or in combination with one or more vitamin (X, XI, XII, and/or XIII), used in the methods of the present invention, reconstitution of the powder can be done with a suitable aqueous liquid, preferably water. Reconstitutable powders are typically in the form of flowable or substantially flowable particulate compositions, or at least particular compositions that can be easily scooped and measured with a spoon or similar other device, wherein the compositions can easily be reconstituted by the intended user with a suitable aqueous fluid, typically water, to a form a liquid infant formula. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving can vary.

The nutritional formulas used in the methods of the present invention may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Premature infants require additional nutrients to support their growth and are at risk for the diseases related to prematurity. Preterm infants are commonly fed either a commercial infant formula designed specifically for these infants or their own mother's milk. Another means of feeding a preterm infant is to supplement preterm milk, banked term milk, other suitable milk, or infant formula with a milk or formula fortifier. Such supplemented milk or formula can more adequately provide levels of one or more nicotinyl compound (I, II, III, IV, V, VI, VII, VIII, and/or IX), or salt thereof, alone or in combination with one or more vitamin (X, XI, XII, and/or XIII), to meet the needs of these infants.

Compositions for oral formulations useful for delivering an infant dietary supplement composition comprising one or more nicotinyl compound (I, II, III, IV, V, VI, VII, VIII, and/or IX), or salt thereof, alone or in combination with one or more vitamin (X, XI, XII, and/or XIII), that are palatable to infants are known in the art. The infant dietary supplement composition useful for delivering comprising one or more nicotinyl compound (I, II, III, IV, V, VI, VII, VIII, and/or IX), or salt thereof, alone or in combination with one or more vitamin (X, XI, XII, and/or XIII), can be orally administered, for example, with an inert diluents or with an assimilable edible carrier, or it can be enclosed in hard or soft shell gelatin capsules, or it can be compressed into tablets, or it can be incorporated directly with the food of the diet. For oral administration, the infant dietary composition comprising one or more nicotinyl compound (I, II, III, IV, V, VI, VII, VIII, and/or IX), or salt thereof, alone or in combination with one or more vitamin (X, XI, XII, and/or XIII) may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better suited for oral use in infants because these are water-miscible, and thus their oiliness is masked. Such emulsions are well known in the pharmaceutical sciences.

Example 1

Figure 2A:
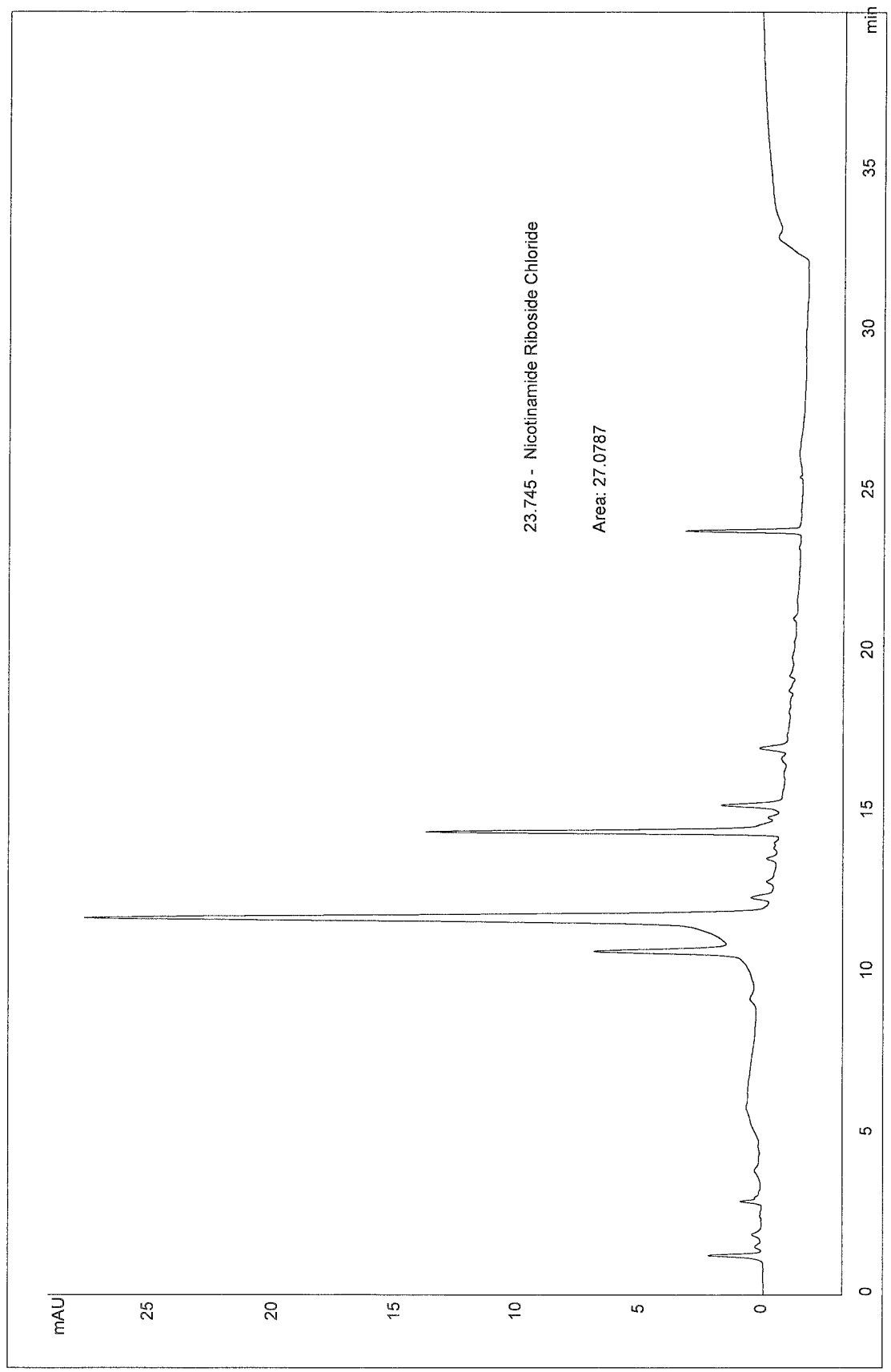
FIG. 2 depicts, in an embodiment, chromatograms demonstrating, comparatively, detection of nicotinamide riboside (NR) present in store bought (cow) milk (FIG. 2A) and detection of nicotinamide riboside (NR) after adding nicotinamide riboside (NR) to the milk sample at a known amount (FIGS. 2B and 2C).
Figure 2B:
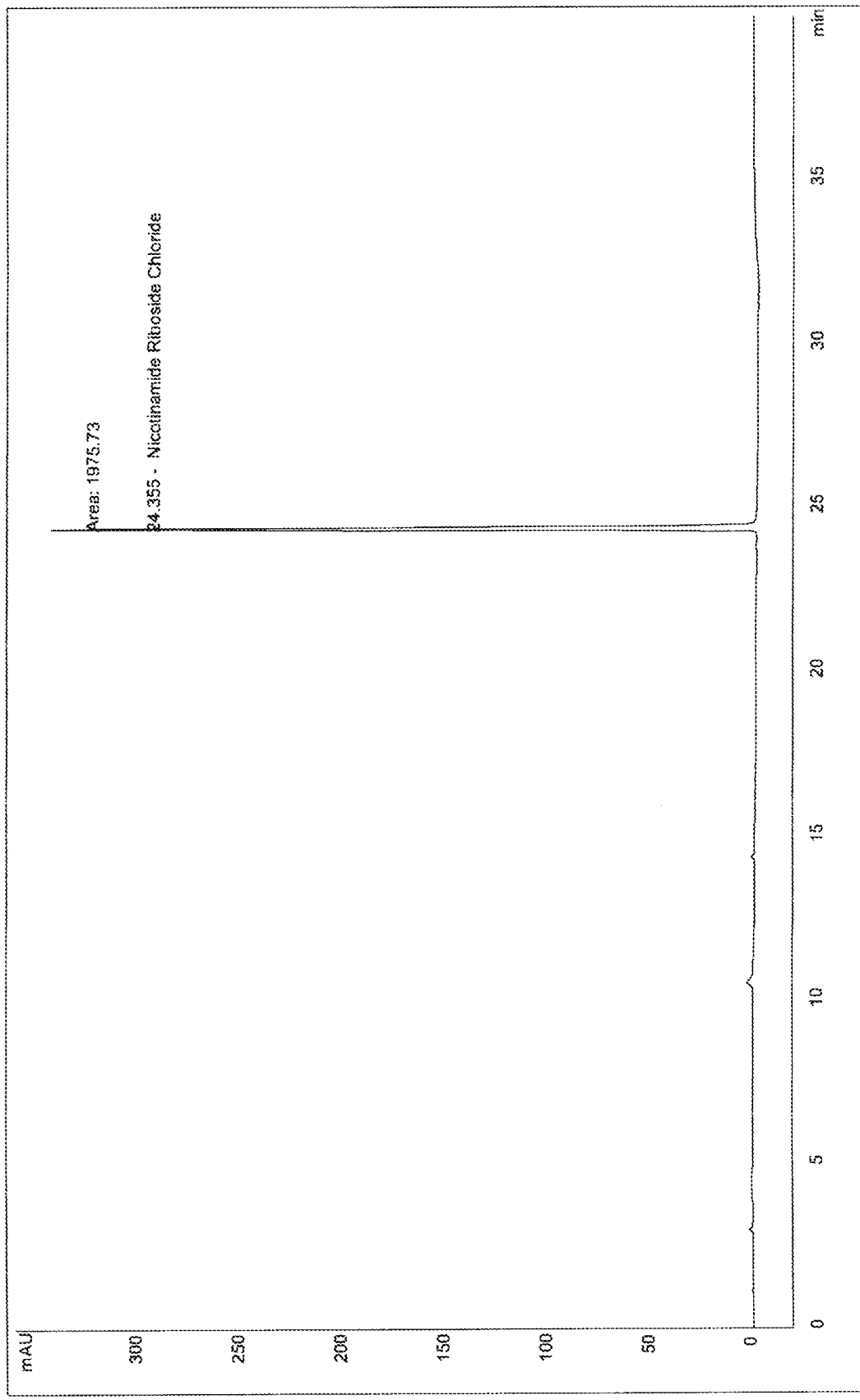
Figure 2C:
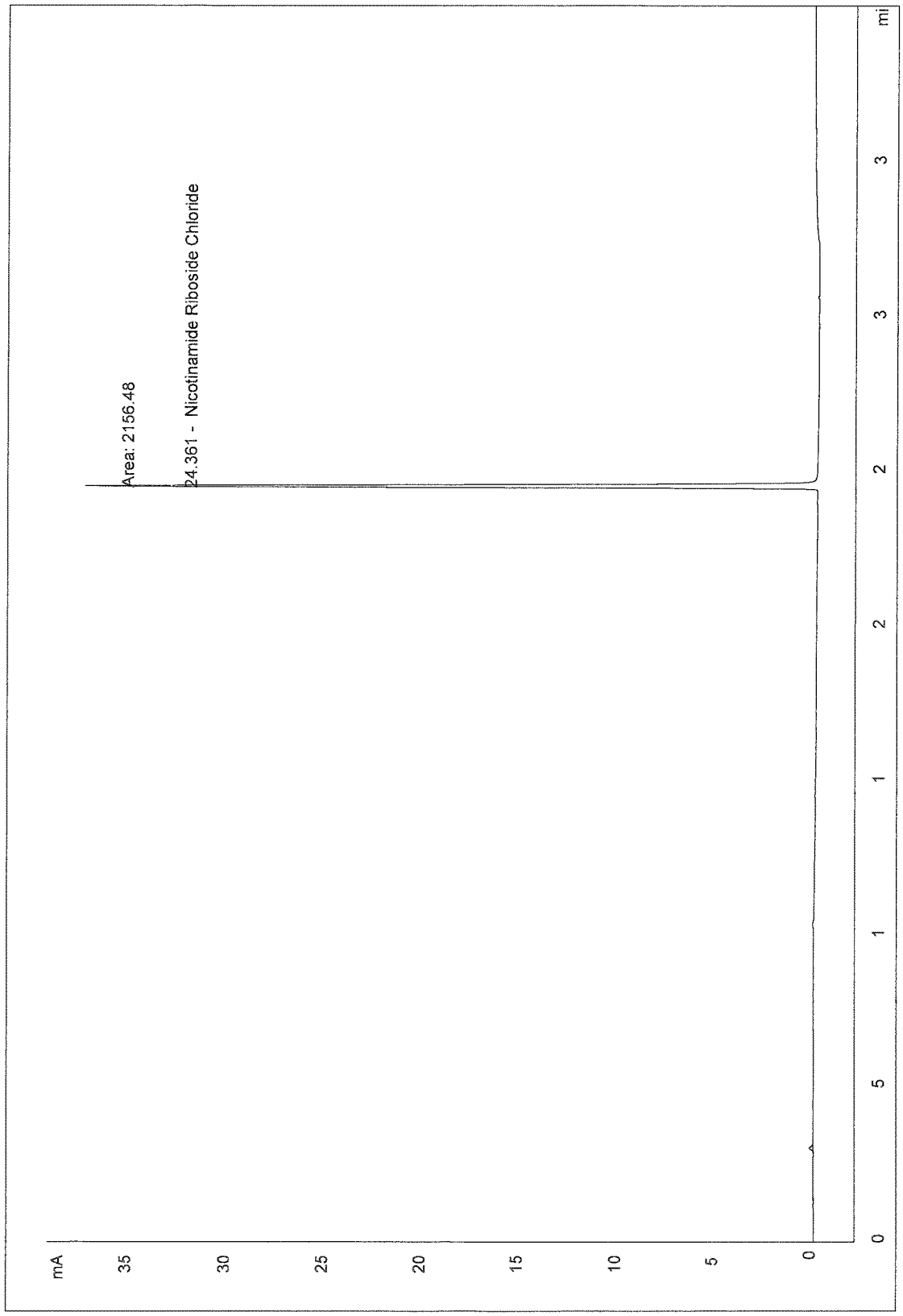

Nicotinamide riboside (NR, I) is also naturally found in milk. FIG. 2 demonstrates that nicotinamide riboside (NR, I) is present in store bought (cow) milk. FIGS. 2B and 2C are control chromatograms showing detection of nicotinamide riboside (NR, I) after adding nicotinamide riboside (NR, I) to the milk sample at a known amount. These control chromatograms demonstrate that nicotinamide riboside (NR, I) could be added to milk and subsequently quantitatively recovered without significant degradation or evidence of incompatibility of nicotinamide riboside (NR, I) with commercial milk. The calculated recovery of the 1% nicotinamide riboside (NR, I) was close to 100%. The experimental method used to obtain these results was as follows: milk was diluted 1:1 with acetonitrile. Centrifugation was then performed to remove any precipitate, and the supernatant was analyzed using an HILIC/HPLC/UV using standard methods.

Figure 3:
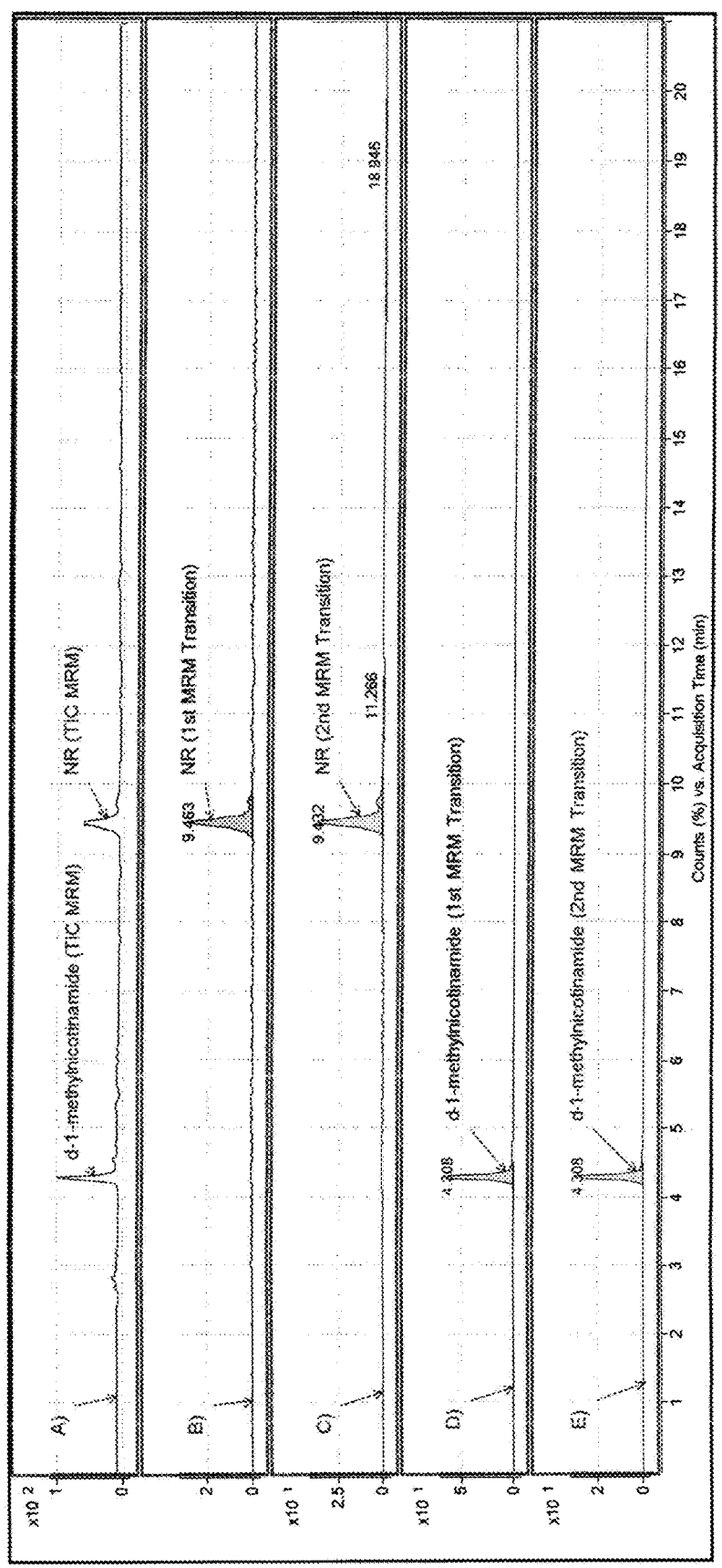
FIG. 3 depicts, in another embodiment, detection of native nicotinamide riboside (NR) in human breast milk.

Nicotinamide riboside (NR, I) is also naturally found in human breast milk. Although previously unpublished, FIG. 3 demonstrates that nicotinamide riboside (NR, I) is present in human breast milk. Fresh frozen human breast milk from a single donor was obtained and analyzed for the presence of nicotinamide riboside (NR, I). Milk was precipitated using acetonitrile with a ratio of 3:1, and acetic acid was also added to help precipitation. Separation was done on a Sepax Polar-Diol (250×4.6 mm) 5 μm column, and the Agilent 6420 Triple Quad system. The mass spectrometer was operated in highly selective and sensitive Multiple Reaction Monitoring ("MRM"). Compound identification was achieved by monitoring two MRM transitions for each of nicotinamide riboside (NR, I) and ISTD (deuterated 1-methylnicotinamide). Specifically, milk sample was mixed very well, after which 2 mL of milk was pipetted into a 15-mL centrifuge tube, and 6 mL of acetonitrile and 1.75 mL of 0.1% acetic acid was added. Finally, 250 μL of ISTD was added. The mixture was vortexed for 1 minute, placed on a shaker for 15 minutes, and centrifuged for 10 minutes at 15000 rpm. The top layer was decanted into a 10-mL volumetric flask and brought to volume with acetonitrile. Sample was then run on HPLC/MS/MS. Spiked samples were prepared and analyzed the same way, except that only 0.75 mL of 0.1% acetic acid was added along with 1 mL of the nicotinamide riboside (NR, I) standard. FIG. 3 shows detection of native nicotinamide riboside (NR, I) in human breast milk by mass in panel A, and by two transitions; B) 255.1 to 123.1, and C) 255.1 to 105.8. Two transitions are also shown for the internal standard (panels D and E).

Figure 4:
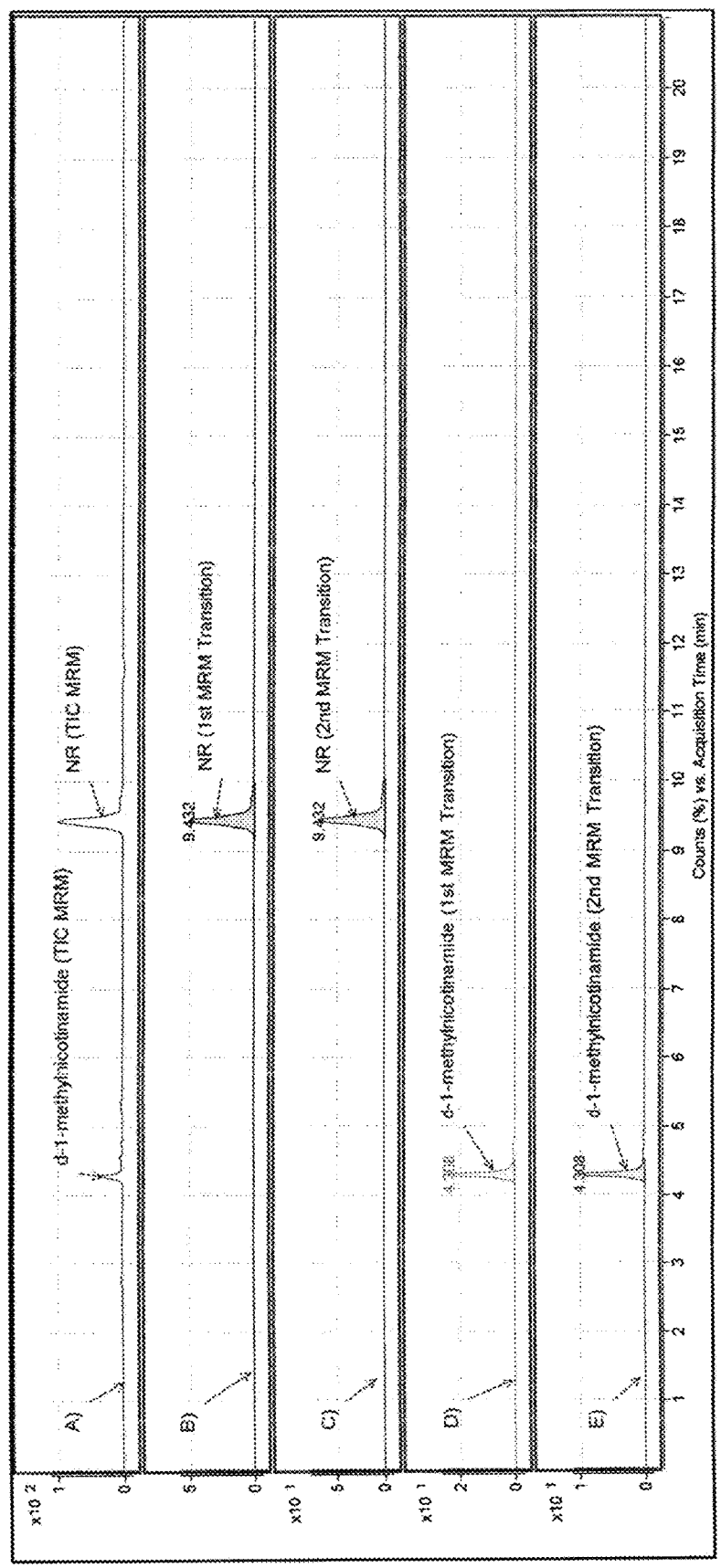
FIG. 4 depicts, in another embodiment, confirmation of detection of nicotinamide riboside (NR) in human breast milk by spiking nicotinamide riboside (NR) at 100 mL.
Figure 5:
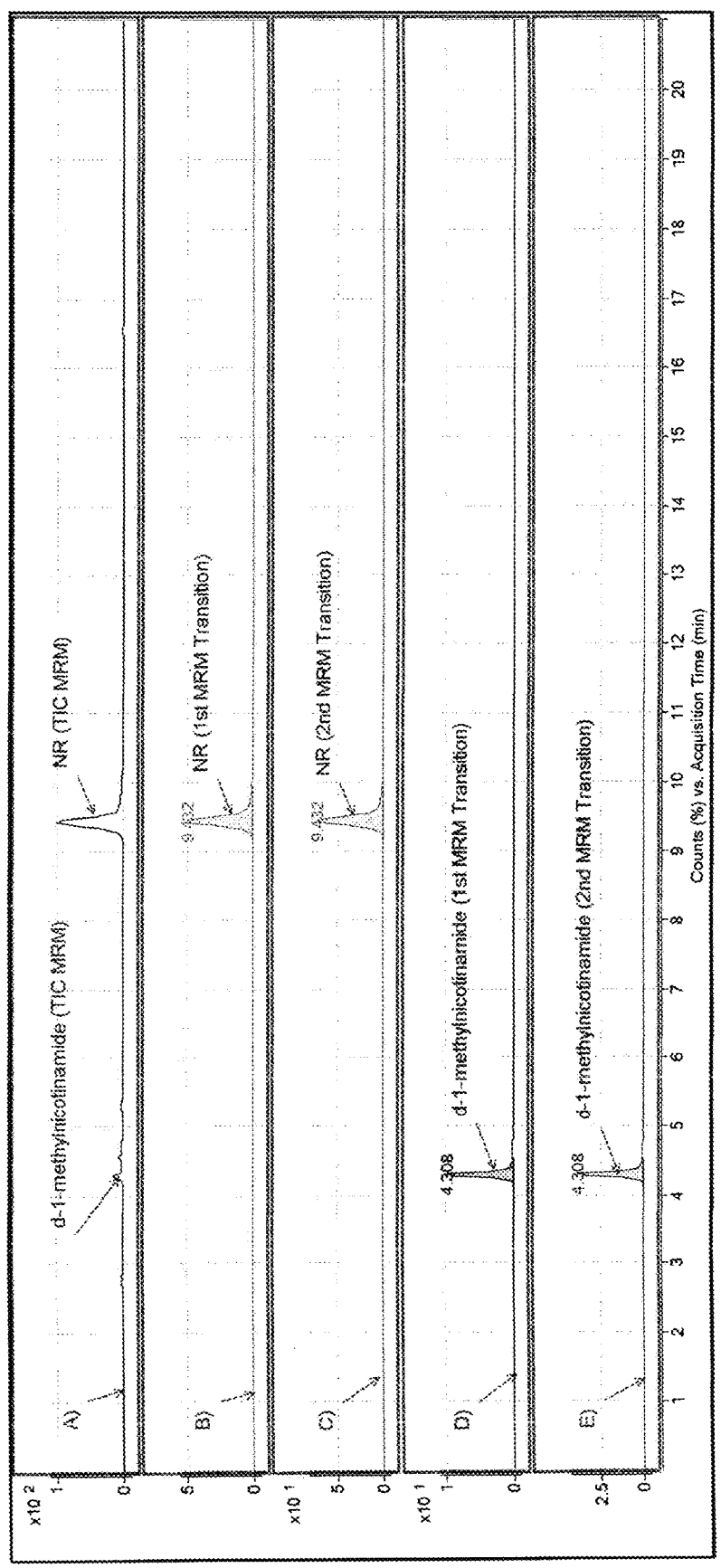
FIG. 5 depicts, in another embodiment, confirmation of detection of nicotinamide riboside (NR) in human breast milk by spiking nicotinamide riboside (NR) at 1000 mL.

FIGS. 4 and 5 are controls that show that spiking of nicotinamide riboside (NR, I) at 100 mL (FIG. 4) and 1000 mL (FIG. 5) confirm that the peaks being analyzed are nicotinamide riboside (NR, I) in panels A, B, and C of both figures. Panels D and E in both figures are the internal standard peaks.

Figure 6:
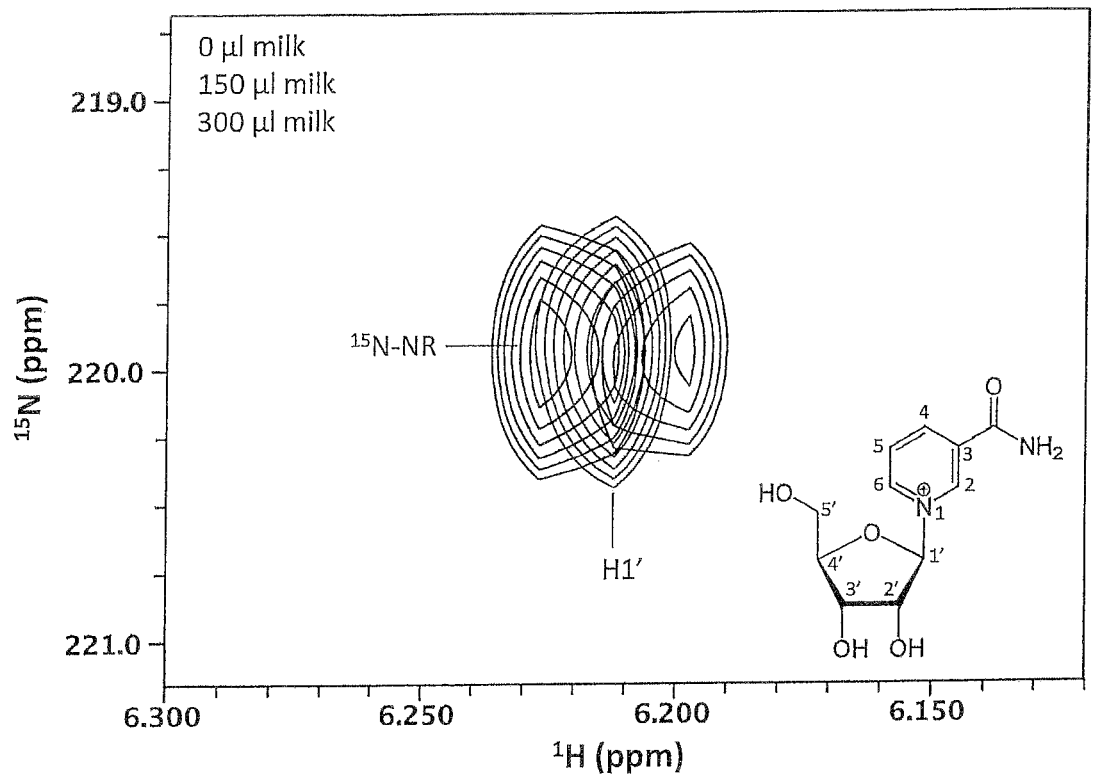
FIG. 6 depicts, in another embodiment, detection of direct binding of stable, isotope-labeled ($^{15}N$) nicotinamide riboside (NR) to milk proteins.
Figure 7:
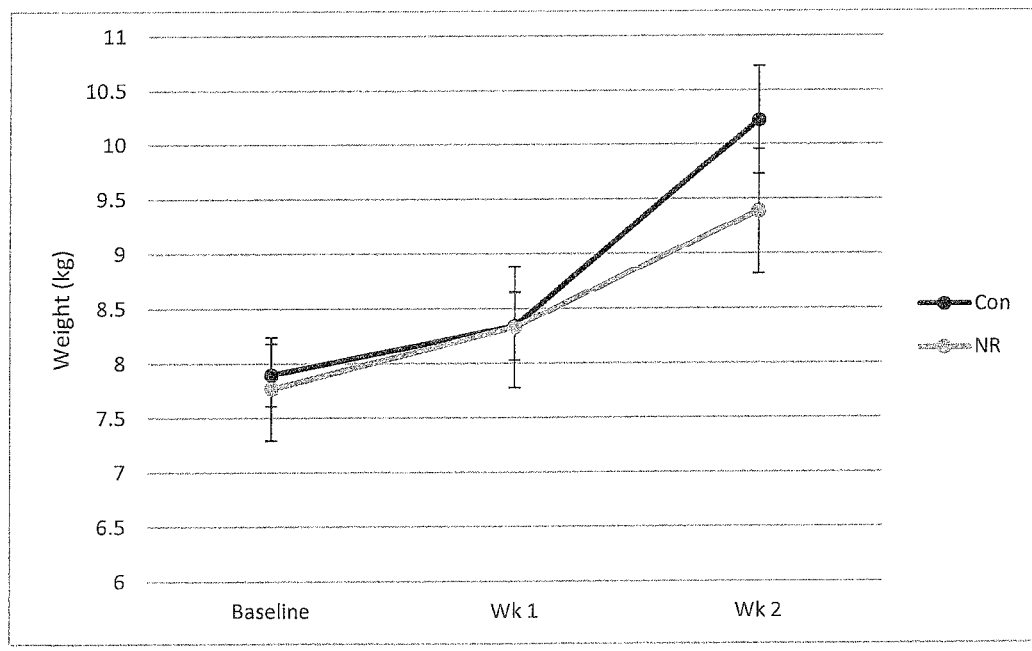
FIG. 7 depicts, in another embodiment, comparison of the weights of piglets administered a control solution to the weights of piglets administered a nicotinamide riboside (NR) solution over time.
Figure 8:
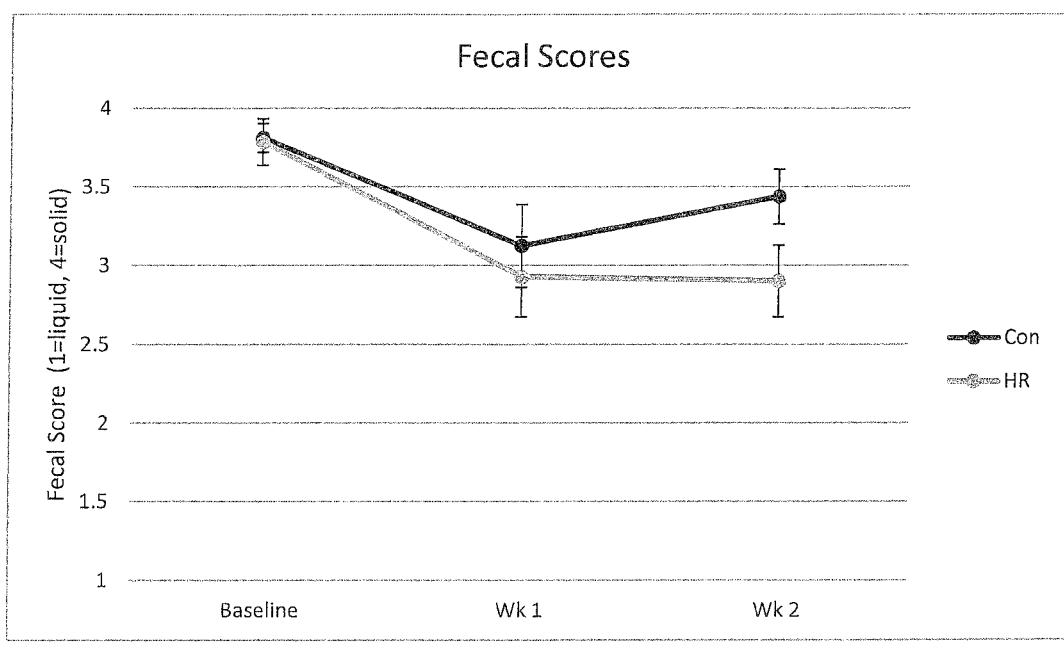
FIG. 8 depicts, in another embodiment, comparison of the fecal scores of piglets administered control solution to the fecal scores of piglets administered a nicotinamide riboside (NR) solution over time.
Figure 9:
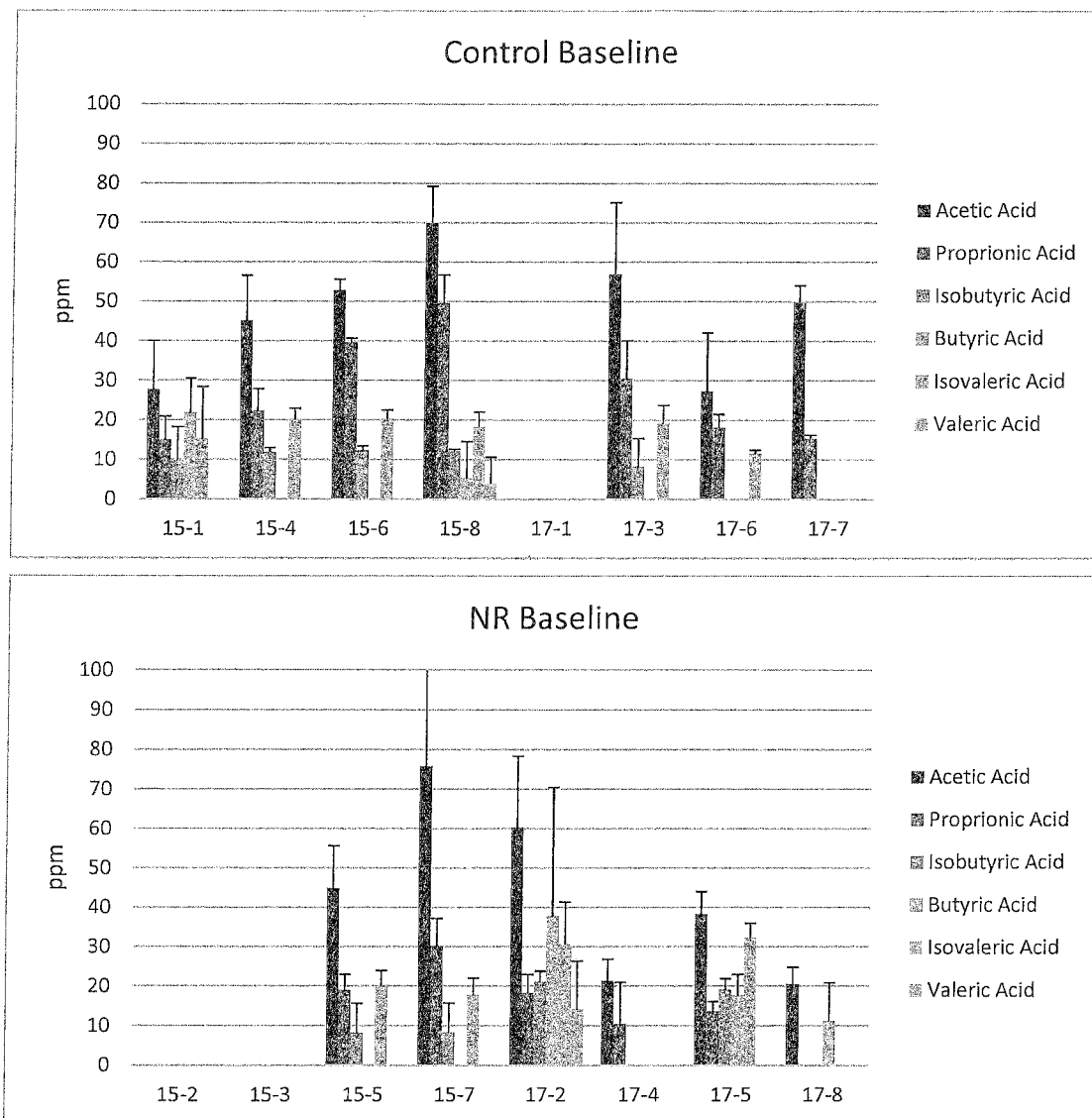
FIG. 9 depicts, in another embodiment, the baseline fecal short chain fatty acid ("SCFA") distribution of piglets administered a control solution (top panel) and baseline fecal SCFA distribution of piglets administered a nicotinamide (NR) solution (bottom panel).
Figure 10:
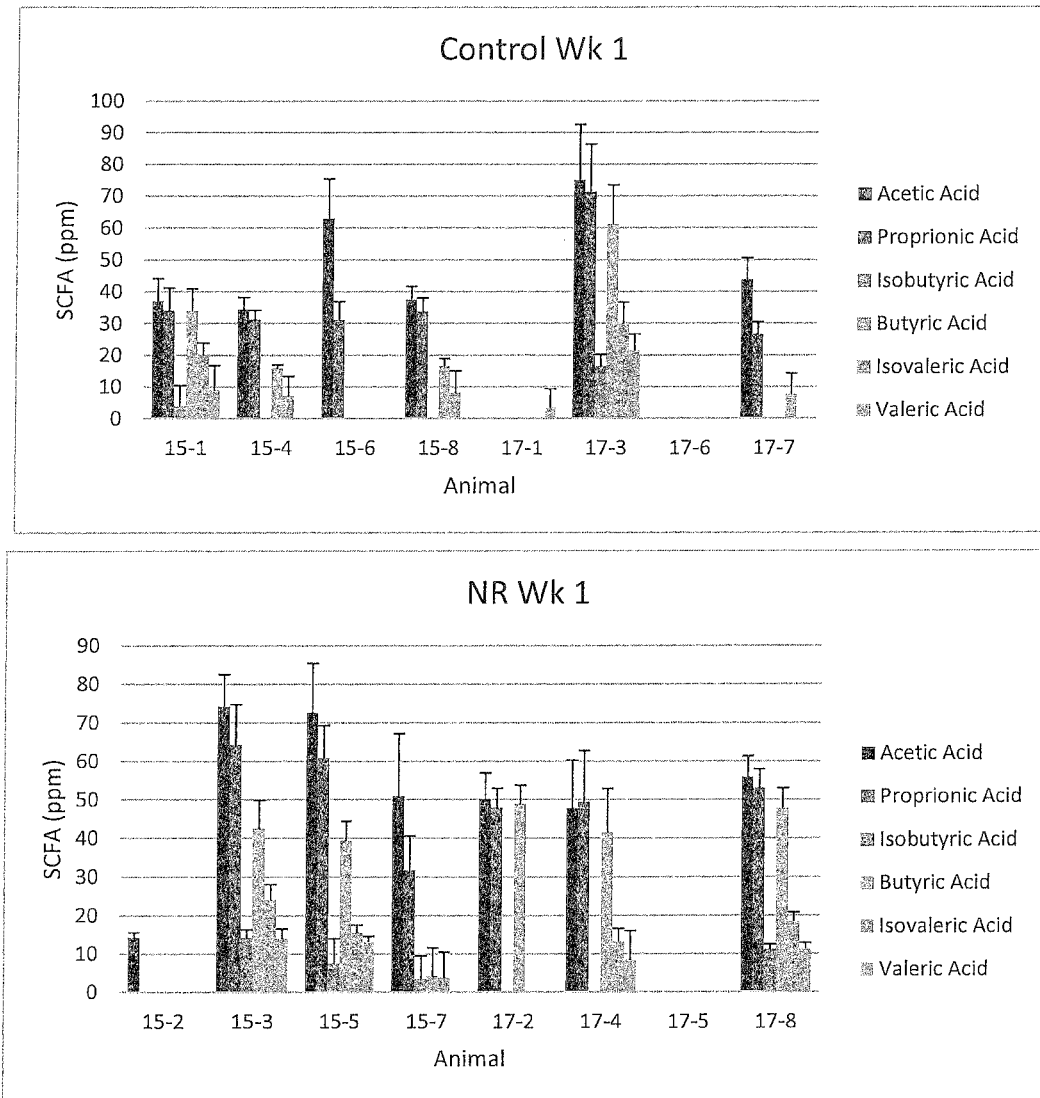
FIG. 10 depicts, in another embodiment, the Week 1 fecal SCFA distribution of piglets administered a control solution (top panel) and Week 2 fecal SCFA distribution of piglets administered a nicotinamide riboside (NR) solution (bottom panel).
Figure 11:
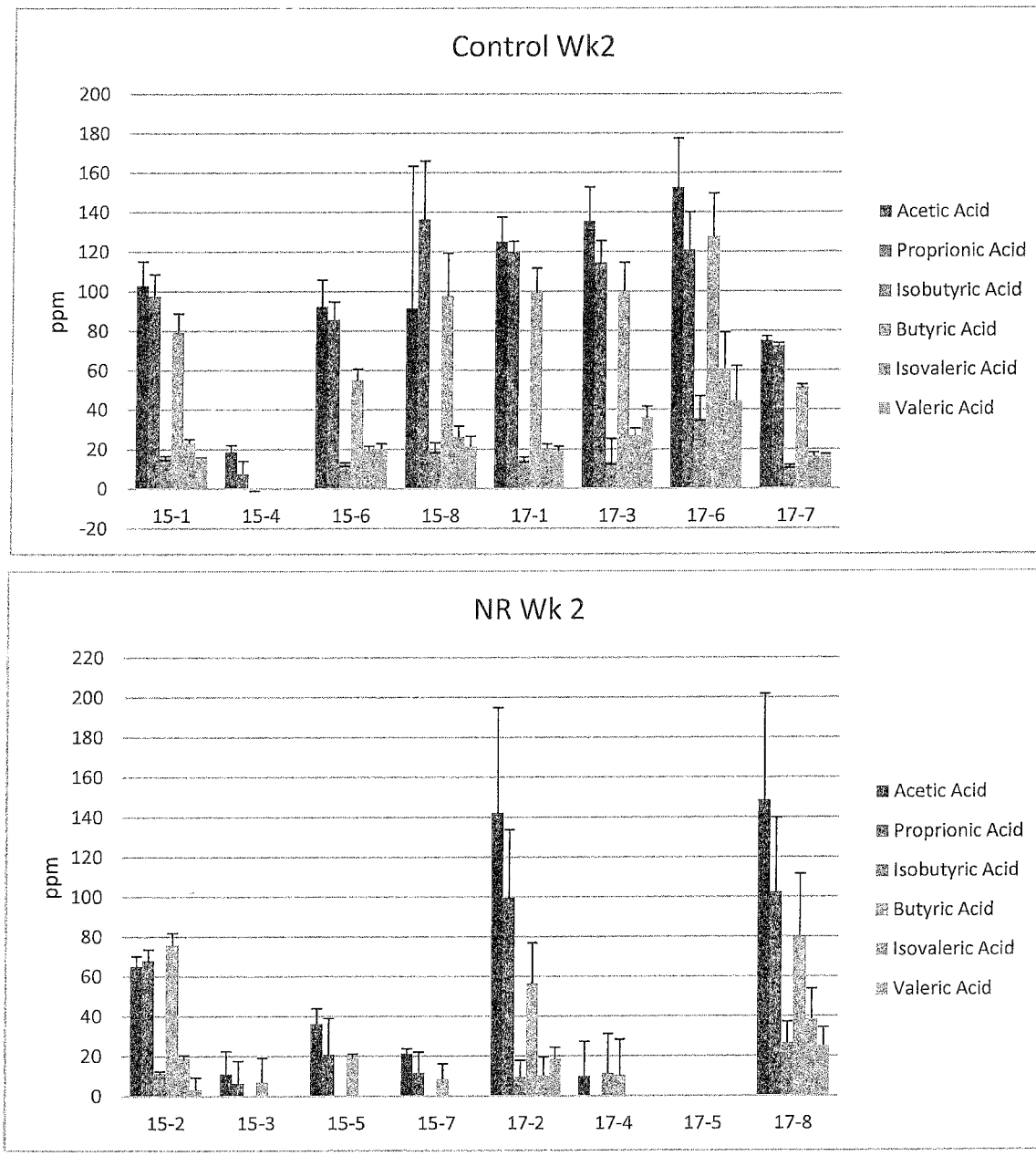
FIG. 11 depicts, in another embodiment, the Week 2 fecal SCFA distribution of piglets administered a control solution (top panel) and Week 2 fecal SCFA distribution of piglets administered a nicotinamide riboside (NR) solution (bottom panel).

Although nicotinamide riboside (NR, I) in water is unstable over time (it will be nicotinamide and ribose given enough time), nicotinamide riboside (NR, I) is stable in milk, as shown above that nicotinamide riboside (NR, I) is present in cow's milk and human breast milk. Nicotinamide riboside (NR, I) is also demonstrated to bind proteins in milk that stabilize nicotinamide riboside (NR, I) in liquid. Whey protein fraction and casein protein have been identified as leading candidates to bind directly to and stabilize nicotinamide riboside (NR, I) in milk. The addition of these proteins in particular (either alone or in combination with other proteins) in order to stabilize nicotinamide riboside (NR, I) in liquid constitutes another embodiment of a method of delivery of the present invention. FIG. 6 shows that nicotinamide riboside (NR, I) binds to proteins in milk. In this experiment, Water-Ligand Observed via Gradient Spectroscopy (WaterLOGSY NMR) was used to detect direct binding of stable, isotope-labeled ($^{15}$N) nicotinamide riboside (NR, I) to milk proteins. This is visualized as a concentration-dependent shift in the nicotinamide riboside (NR, I) spectra with increasing additions of milk. The concentric shapes shifts from left to right are the results of addition of no milk, 150 mL of milk, and 300 mL of milk, respectively.

Example 2

The Role of Nicotinamide Riboside (NR, I) in Protecting the Fragile Neurologic Development in the Piglet Gut as a Model for Human Infants
Introduction
Human infants are born developmentally immature. This is especially true of their neurological tissues in which over one third of brain growth occurs in the first 6 months of life after birth. Brain growth is known to place a massive demand on nourishment, with human milk having to provide all of the substrates to assemble and fuel this brain development. Research now indicates that sufficient essential nutrients are not enough to support optimal brain growth and development. Eccentric demands of other tissues during development can compromise brain growth.

The liver, kidney, and intestine are sites of glucose production via gluconeogenesis for the body to maintain proper blood glucose levels. In the immature gut of a developing mammal, intestinal gluconeogenesis occurs at a greater rate than in an adult. See P. Hahn & H. Wei-Ning, Gluconeogenesis from Lactate in the Small Intestinal Mucosa of Suckling Rats, 20 PEDIATRIC RESEARCH 1321 (1986), incorporated by reference herein in its entirety. NADH is required for gluconeogenesis to occur and the high intra-mitochondrial ratio of NADH to NAD$^+$ in the intestine results in decreased intestinal oxidation that may spare glucose for other organs such as the brain. See R. H. Lane et al., *IGF alters jejunal glucose transporter expression and serum glucose levels in immature rats*, 283 AM. J. PHYSIOLOGY—REGULATORY, INTEGRATIVE & COMPARATIVE PHYSIOLOGY R1450 (2002), incorporated by reference herein in its entirety. Newborns exhibit marked increases in specific brain region glucose metabolism correspondent with improved skill development and hearing. See H. T. Chugani, *A Critical Period of Brain Development: Studies of Cerebral Glucose Utilization with PET*, 27 PREVENTIVE MEDICINE 184 (1998), incorporated by reference herein in its entirety. Increasing the availability of nicotinamide adenine nucleotides to the intestine may increase its gluconeogenic potential, which will increase the availability of glucose for optimal brain development.

During the early postnatal period, the enteric nervous system ("ENS") forms. In early development, the bowel continues to grow in length and diameter likely involving the generation of new neurons. See P. Hahn & H. Wei-Ning, 1986. Two particularly important signaling molecules for ENS development are glial cell line-derived neurotrophic factor ("GDNF") and Neurturin. GDNF controls ENS precursor proliferation and therefore has significant influence over the number of enteric neurons. Maintaining the size of mature enteric neurons and the extent of neuronal projections is the job of Neurturin. See R. H. Lane et al., 2002. The formation of the ENS is dependent upon the transmembrane tyrosine kinase Ret whose absence significantly reduces gut contractility. See id. furthermore, in rats that are heterozygous for GDNF, Ret, or knockout for Neurturin, the major enteric signaling molecules vasoactive intestinal peptide ("VIP") and substance P are reduced. See id. At birth, the mammalian vagus nerve, which plays a crucial role in relaying information from the gut to the brain, is only partially myelinated and development continues during the first few months postpartum. See H. T. Chugani, 1998. Properly functioning vagal afferents are necessary for gut microbes to modulate the gut-brain-microbiome axis. E. A. Maga et al., *Consumption of lysozyme-rich milk can alter microbial fecal populations*, 78 APPL. ENVIRON. MICROBIOL. 6153 (2012), incorporated by reference herein in its entirety.

Nicotinamide (Nam or NM) has been shown to upregulate peroxisome proliferator-activated receptor-γ coactivator 1-α ("PGC1α"). See C. A. Cooper et al., Lysozyme transgenic goats' milk positively impacts intestinal cytokine expression and morphology, 20 TRANSGENIC RESEARCH 1235 (2011), incorporated by reference herein in its entirety. PGC1α is a transcriptional coactivator of genes for the proteins that regulate mitochondrial biogenesis and function as well as a participant in modulating the switch in cells from glycolytic to oxidative metabolism. See D. R. Brundige et al., *Consumption of pasteurized human lysozyme transgenic goats' milk alters serum metabolite profile in young pigs,* 19 TRANSGENIC RESEARCH 563 (2010), incorporated by reference herein in its entirety. PGC1α is highly expressed in the apically located differentiated intestinal epithelial cells where it supports proper intestinal functioning and metabolism. See id.

The piglet as a model of human infants and the intestinal microbiological similarities The piglet has become the model of choice for infant intestinal development and illness. Proof-of principle work in healthy young pigs demonstrated that consumption of lysozyme-rich milk beneficially modulates fecal microbiota composition by enriching for microbes considered biomarkers of gut health (Bifidobacteriaceae and Lactobacillaceae) while reducing those associated with disease, much like human milk. See E. A. Maga et al., 2012. The shift in microbiota was accompanied by changes in both gut architecture and gene expression, indicating improvements in both the digestive and immunoprotective functions of the intestine. These changes included increased intestinal surface area (longer villi and thinner lamina propria) implying increased absorptive function, increased expression of an anti-inflammatory gene (TGF-β) and positive changes in circulating metabolites. See C. A. Cooper et al., 2011; D. R. Brundige et al., 2010. Lactoferrin-rich milk had more modest effects on bacterial populations (unpublished data) but larger effects on promoting increased intestinal surface area and the dampening of inflammation. See C. A. Cooper et al., *Consumption of transgenic cows' milk containing human lactoferrin results in beneficial changes in the gastrointestinal tract and systemic health of young pigs,* 22 TRANSGENIC RESEARCH 571 (2012), incorporated by reference herein in its entirety.

The efficacy of lysozyme and lactoferrin-rich milk to influence disease, has been successfully documented in the piglet via models of bacterial-induced diarrhea and malnutrition. The central paradigm of each of these models (challenge with enterotoxigenic *E. coli* ("ETEC") and protein and calorie restriction, respectively) is the devastating consequences of microbiota dysbiosis along the length of the gastrointestinal tract and damage to the intestinal epithelium. The power of these models to detect successful intervention is highlighted by the results with lysozyme-rich milk. This simple addition of a well characterized milk component, to milk, served as an effective treatment for alleviating the clinical symptoms of diarrhea, returned levels of circulating immune cells to normal and accelerated recovery of intestinal structure. See C. A. Cooper et al., *Consuming transgenic goats' milk containing the antimicrobial protein lysozyme helps resolve diarrhea in young pigs,* 8 PLOS ONE e58409 (2013), incorporated by reference herein in its entirety. Cow's milk was shown to be an effective agent with which to begin to reverse structural and functional damage to the intestine caused by malnutrition with lactoferrin-rich cow milk improving many aspects of the condition of the intestine over milk alone. See L. C. Garas et al., *Milk with and without lactoferrin can influence intestinal damage in a pig model of malnutrition,* 7 FOOD & FUNCTION 665 (2016), incorporated by reference herein in its entirety. Both milks were able to positively influence weight gain, blood chemistry and intestinal morphology, permeability and gene expression, as well as microbiota populations. The considerable development of the piglet as an intestinal model of infants has made it possible to take a broad, systems biology approach relating the interactions between the microbiome, microbial transcriptome, metabolome, and the host intestinal transcriptome to intestinal structure and function.

The study was proposed to measure markers of energy metabolism in piglets weaned 7 days early in order to understand the role of nicotinamide riboside (NR, I) for improving intestinal and systemic energy metabolism, tissue growth, and neurological development in infancy. Achieving these aims will provide a mechanistic framework to support the addition of nicotinamide riboside (NR, I) to human infant formula.

Specific Aims

This study addresses the need to understand the role of nicotinamide riboside (NR, I) in supporting energy metabolism at the level of the gut during infancy on the background of typical intestinal dysbiosis that is known to occur in both piglets that have an abrupt dietary shift, and humans who have a more gradual dietary shift when weaned from mother's milk. See S. A. Frese et al., *Diet shapes the gut microbiome of pigs during nursing and weaning,* 3 MICROBIOME 28 (2015); J. B. Koenig et al., *Succession of microbial consortia in the developing infant gut microbiome,* 108 PROCEEDINGS NAT'L ACAD. SCI. 4578 (2011); each of which is incorporated by reference herein in its entirety. This animal model has been used to define the relationship between oligosaccharides in human milk and the infant microbiome. Failure to establish a *B. infantis* dominated microbiome during infancy has been shown to result in a chronic inflammatory state. It was expected that consuming nicotinamide riboside (NR, I) would support production of energy through microbial fermentation to provide a source of energy for colonocytes, enhance appropriate fueling of intestinal processes, and maintain neurogenesis, all of which ultimately promote health and lower disease risk throughout lifespan. The specific aims were to: (1) characterize the effect of nicotinamide riboside (NR, I) supplementation on key parameters of growth and development, such as weight gain, growth, feed efficiency ratio, stool consistency, and activity levels; (2) characterize the intermediates and functioning of energy metabolism within the gut, such as by analyzing the metabolites in blood and feces as a measurement of metabolism within the intestine and evaluating the differences due to nicotinamide riboside (NR, I) supplementation.

It was expected that this study would (a) provide data as to the role of nicotinamide riboside (NR, I) in growth, development, and gut energy and microbiota health in the weanling piglet; (b) advance our understanding of how the availability of a potent $NAD^+$ precursor, nicotinamide riboside (NR, I), impacts energy metabolism in the gut and influences markers of neurogenesis; and (c) further validate the weanling piglet as a model for gut-brain axis and the importance of energy metabolism during infancy.

Methods

Animals

Sixteen (n=16) Yorkshire/Hampshire crossbred piglets were obtained from the University of California, Davis Swine Teaching and Research Center and received on lactation day ("LD") 14. Prior to arrive, the piglets were processed by the suppler between 1-3 days of age by administration of iron and an antibiotic (Excede for swine) as is common practice at the University of California, Davis Swine Facility. It is not common practice at the University of California, Davis Swine Facility to give a second dose of iron and antibiotics unless it becomes necessary.

The piglets were from two litters (litters 15 and 17), weaned at 17 days of age, and randomly placed into one of two groups balanced for litter, sex, and weight. See Table 1. The animals were not acclimated to the facility at arrival and were subsequently acclimated to the test diet administration system. The piglets were weaned into a temperature-controlled room (approximately 27-29° C.) that contained 10 adjacent pens. The piglets were group-housed in the nursery room at the Swine Facility, which is an enclosed room with access restricted to trained personnel. The two groups were separated by one pen containing piglets of similar age.

TABLE 1

Distribution of pigs into experimental groups

| Control Group | | | Nicotinamide Riboside (NR, I) Group | | |
| --- | --- | --- | --- | --- | --- |
| Pig # | Sex | Initial Wt (kg) | Pig # | Sex | Initial Wt (kg) |
| 15-1 | F | 9.52 | 15-2 | F | 6.35 |
| 15-4 | M | 7.26 | 15-3 | F | 9.07 |
| 15-6 | M | 8.39 | 15-5 | M | 7.26 |
| 15-8 | M | 8.12 | 15.7 | M | 10.43 |
| 17-1 | F | 7.71 | 17-2 | F | 7.71 |
| 17-3 | F | 7.26 | 17-4 | F | 6.8 |
| 17-6 | M | 6.98 | 17-5 | M | 7.26 |
| 17-7 | M | 7.94 | 17-8 | M | 7.26 |
| Average Wt (kg) | | 7.9 ± 0.8 | | | 7.8 ± 1.3 |

Each morning enough nicotinamide riboside (NR, I) in water solution was prepared for that day's dose administration according to the dose preparation protocol. At least 5 mL of prepared dose was reserved and immediately frozen after preparation each day for analysis of nicotinamide riboside (NR, I) for the purpose of confirming stability of the dose material. The doses were stored at refrigeration temperature while not in use. Nicotinamide riboside (NR, I) was dosed once per day in the morning and at the same time each day. Piglets in the control group received the same volume of plain water and were dosed on the same schedule.

The daily amount of nicotinamide riboside (NR, I) approximated the dose (33 mg/kg) used in human investigations of efficacy in areas of mitochondrial dysfunction converted to piglet equivalent dose using the body surface area method. See A. B. Nair & S. Jacob, *A simple practice guide for dose conversion between animals and human*, 7 J. BASIC CLIN. PHARMA 27 (2016), incorporated by reference herein in its entirety.

Starting on Day 1, animals in the nicotinamide riboside (NR, I) group were dosed once daily (in the morning) with 277 mg nicotinamide riboside (NR, I) per pig resuspended in water for seven days. After one week, animals were dosed once daily with 342 mg nicotinamide riboside (NR, I) per pig delivered in 2.5 mL for seven days. For Days 1 and 2, the nicotinamide riboside (NR, I) solution was prepared by resuspending 2770 mg nicotinamide riboside (NR, I) in 50 mL water, and 5 mL of this solution was delivered to each pig by squirting it into the back of the mouth using a 10 mL syringe with a piece of tubing attached to the end. To reduce the volume to more efficiently deliver the nicotinamide riboside (NR, I) solution, the 2770 mg was resuspended in 25 mL water and 2.5 mL of the solution was squirted into the back of the mouth of each pig using a 3 mL syringe for Days 3-7. For Days 8-14, 3420 mg nicotinamide riboside (NR, I) was resuspended in 25 mL water and 2.5 mL of this solution was delivered to each pig. Each day prior to dosing, 2.5 mL of the nicotinamide riboside (NR, I) (5 mL on Days 1 and 2) were placed into a separate tube and frozen.

Weights, and Fecal and Activity Scores

All animals were weighed at weaning (baseline) and after one and two weeks of nicotinamide riboside (NR, I) supplementation. Fecal and activity scores were recorded daily using the scales listed below. Weights and fecal scores were analyzed using a two-factor repeated measures ANOVA (mixed-model ANOVA) with p values <0.05 considered significant. The fecal consistency scale used is as follows: 4=normal (solid); 3=soft feces (semi-solid); 2=mild diarrhea (semi liquid); 1=severe diarrhea (liquid). The activity level scale used is as follows: 4=alert, attentive (moving, eating, drinking, clear eyes); 3=alert, less active (moves in response to presence, but not far, eating and drinking, clear eyes); 2=somewhat lethargic, tired (makes noise but does not stand, some interest in food and water, bouts of shivering, some glassy, puffy eyes); 1=very lethargic (unwilling to stand, uninterested in food and water, persistent shivering, glassy, puffy eyes).

Blood Collection and Analysis

Blood was collected from each pig via jugular venipuncture on Days 1, 8, and 14. In each instance, blood was collected prior to dosing with nicotinamide riboside (NR, I). On Day 1, the sow was removed from the piglets for approximately three hours prior to sample collection. On Days 8 and 14, feed was removed from the animals' pens 12 hours prior to sample collection. Blood was collected into purple-top vacutainers for CBC analysis and into red-top vacutainers for blood chemistry analysis. CBC analysis was performed at IDEXX Laboratories in West Sacramento, Calif. using the Sysmex XT-iV Vet Hematology Autoanalyzer (Sysmex America Inc., Lincolnshire, Ill.). Red-top tubes were spun to collect serum and the serum frozen. Frozen aliquots (500 µL) were submitted to the University of California, Davis Veterinary medicine Teaching Hospital Clinical Diagnostic Laboratory for Blood Chemistry Analysis using the Cobas 6000 C501 Clinical Chemistry Analyzer (Roche Diagnostics, Indianapolis, Ind.). Aliquots of the remaining frozen serum will be used for serum metabolite analysis. CBC and blood chemistry parameters were analyzed using a two-factor ANOVA (treatment and time) accounting for repeated measures (mixed-model ANOVA). p-values <0.05 were considered significant. Reference intervals for both 6-week old pigs (Cooper et al., 5 J. ANIM. SCI. BIOTECHNOL. 5 (2014), incorporated by reference herein in its entirety) and pigs in general (supplied by University of California, Davis Veterinary Testing Laboratory) are shown in Table 2.

TABLE 2

Reference intervals for pigs

| | 6 Week Old Pigs | Pigs Generally |
| --- | --- | --- |
| CBC | | |
| RBC, M/µL | 5.5-9.1 | |
| HGB, g/dL | 8.8-12.7 | |
| HCT, % | 28.3-42.7 | |
| MCV, fL | 38.4-59.3 | |
| MCH, pg | 11.1-18.4 | |
| MCHC, g/dL | 27.9-32.4 | |
| WBC, × $10^3$ cells/µL | 5.44-25.19 | |
| Neutrophils, × $10^3$ cells/µL | 0.81-13.40 | |
| Lymphocytes, × $10^3$ cells/µL | 3.81-14.92 | |
| Monocytes, cells/µL | 219-1705 | |
| Eosinophils, cells/µL | 45-481 | |
| Basophils, cells/µL | 14-146 | |

TABLE 2-continued

Reference intervals for pigs

| Blood Chemistry | 6 Week Old Pigs | Pigs Generally |
|---|---|---|
| Anion Gap, mmol/L | 14-29 | 13-27 |
| Sodium, mmol/L | 131-151 | 141-152 |
| Potassium, mmol/L | 3.7-6.1 | |
| Chloride, mmol/L | 93-108 | 97-110 |
| Bicarbonate, mmol/L | 19-31 | 23-34 |
| Phosphorus, mg/dL | 6.3-11.5 | 7.1-10.2 |
| Calcium, mg/dL | 9.9-12.5 | 8.9-10.3 |
| BUN, mg/dL | 4-18 | 7-14 |
| Creatinine, mg/dL | 0.5-1.1 | 1.2-2.3 |
| Glucose, mg/dL | 75-136 | 43-104 |
| Total Protein, g/dL | 4-5.8 | 5.7-7.6 |
| Albumin, g/dL | 3.1-4.8 | 2.2-4.2 |
| Globulin, g/dL | 0.3-1.7 | |
| AST, U/L | 13-111 | |
| Creatine Kinase, × $10^3$ U/L | 0.15-5.43 | 0.26-0.91 |
| Alkaline Phosphatase, U/L | 130-513 | 49-289 |
| GGT, U/L | 33-94 | 11-56 |
| Bilirubin Total, mg/dL | 0.0-0.2 | 0.0-0.3 |

Fecal Collection and Analysis of SCFA

Fresh fecal samples were collected from each pig on Days 1 (baseline), 8 (Wk 1), and 14 (Wk 2), and frozen. When a freshly voided sample could not be obtained, the rectum was swabbed. A total of 100 mg of feces from each pig was used for SCFA analysis using gas chromatography with known standards for acetic acid, propionic acid, isobutyric acid, butyric acid, isovaleric acid, and valeric acid. Samples were extracted with 25% metaphosphoric acid and each extraction run in triplicate on a GC equipped with the PeakSimple Chromatography Data System. Data was analyzed using a one-way ANoVA or the non-parametric Kruskal-Wallis test if the distribution of values was not Gaussian. A conservative analysis of the data is presented below (animals that had to be swabbed to get a fecal sample) in Table 3 and an analysis of the data including the swab samples is in Table 8. The trends are similar, the p-values are not.

TABLE 3

Fecal SCFA analysis without swab samples in control (n = 8) and nicotinamide riboside (NR, I) (n = 8) pigs (Mean ± SD)

| | Baseline | | | Wk 1 | | | Wk 1 | | |
|---|---|---|---|---|---|---|---|---|---|
| | Control | NR | P | Control | NR | P | Control | NR | P |
| Fecal SCFA | | | | | | | | | |
| Acetic Acid, ppm | 47.1 ± 17.6 | 43.5 ± 23.5 | 0.598 | 49.4 ± 19.2 | 55.78 ± 13.4 | 0.301 | 110.7 ± 36.7* | 118.7 ± 55.01* | 0.698 |
| Propionic Acid, ppm | 27.3 ± 13.5 | 15.3 ± 10.6 | 0.004 | 40.3 ± 17.6 | 49.3 ± 13.3* | 0.127 | 106.8 ± 24.8* | 90.0 ± 30.4 | 0.166 |
| Isobutyric Acid, ppm | 7.8 ± 6.3 | 9.5 ± 9.3 | 0.527 | 4.1 ± 7.2 | 5.8 ± 6.5 | 0.504 | 17.4 ± 9.6* | 15.9 ± 10.6* | 0.703 |
| Butyric Acid, ppm | 3.9 ± 8.7 | 11.1 ± 18.4 | 0.141 | 25.5 ± 22.2 | 36.9 ± 18.3 | 0.135 | 87.2 ± 28.5* | 70.8 ± 21.9 | 0.103 |
| Isovaleric Acid, ppm | 15.0 ± 8.4 | 16.8 ± 14.0 | 0.629 | 13.0 ± 11.9 | 11.9 ± 9.8 | 0.772 | 27.5 ± 15.6* | 22.5 ± 15.5 | 0.430 |
| Valeric Acid, ppm | 0.6 ± 2.6 | 2.4 ± 6.9 | 0.306 | 6.1 ± 9.4 | 6.7 ± 6.7 | 0.828 | 24.7 ± 12.3* | 15.7 ± 11.5 | 0.072 |

*Significantly different over time with preceding time point

TABLE 4

P-values over time for SCFA analysis without swab samples

| | Baseline-Wk1 | | Wk1-Wk2 | | Baseline-Wk2 | |
|---|---|---|---|---|---|---|
| | Control | NR | Control | NR | Control | NR |
| Acetic Acid | 0.999 | 0.999 | <0.0001 | 0.0487 | <0.0001 | <0.0001 |
| Propionic Acid | 0.117 | <0.0001 | <0.0001 | <0.0001 | <0.0001 | <0.0001 |
| Isobutyric Acid | 0.643 | 0.643 | <0.0001 | 0.033 | 0.002 | 0.313 |
| Butyric Acid | 0.150 | 0.171 | 0.0003 | 0.365 | <0.0001 | 0.0003 |
| Isovaleric Acid | 0.957 | 0.847 | 0.0095 | 0.298 | 0.0143 | 0.847 |
| Valeric Acid | 0.952 | 0.999 | <0.0001 | 0.573 | <0.0001 | 0.019 |

Body Weight

TABLE 5

Body weight in Control (n = 8) and nicotinamide riboside (NR, I) (n = 8) pigs (Mean ± SD)

| Weight (kg) | Baseline | | | Wk 1 | | | Wk 2 | | |
|---|---|---|---|---|---|---|---|---|---|
| | Control | NR | P | Control | NR | P | Control | NR | P |
| Weight | 7.89 ± 0.81 | 7.77 ± 1.33 | 0.971 | 8.34 ± 0.86* | 8.33 ± 1.56* | 0.999 | 10.22 ± 1.41* | 9.39 ± 1.61* | 0.500 |

*Significantly different over time with preceding time point

Fecal and Activity Scores

TABLE 6

Fecal and activity scores of control (n = 8) and nicotinamide riboside (NR, I) (n = 8) pigs (Mean ± SD)

| | Baseline | | | Wk 1 | | | Wk 2 | | |
|---|---|---|---|---|---|---|---|---|---|
| | Control | NR | P | Control | NR | P | Control | NR | P |
| Fecal Score | 3.81 ± 0.26 | 3.78 ± 0.39 | 0.999 | 3.12 ± 0.74* | 2.93 ± 0.67* | 0.858 | 3.44 ± 0.49 | 2.90 ± 0.60 | 0.162 |
| Activity Score | 4.0 | 4.0 | | 4.0 | 4.0 | | 4.0 | 4.0 | |

*Significantly different over time with preceding time point

CBC and Blood Chemistry Analysis

TABLE 7

CBC and blood chemistry analysis of control (n = 8) and nicotinamide riboside (NR, I) (n = 8) pigs (Mean ± SD)

| | Baseline | | | Wk 1 | | | Wk 2 | | |
|---|---|---|---|---|---|---|---|---|---|
| | Control | NR | P | Control | NR | P | Control | NR | P |
| CBC | | | | | | | | | |
| RBC, M/μL | 6.79 ± 0.43 | 6.45 ± 0.80 | 0.695 | 6.77 ± 0.35 | 6.06 ± 0.85* | 0.140 | 6.63 ± 0.51 | 6.11 ± 0.98 | 0.367 |
| HGB, g/dL | 11.1 ± 1.4 | 10.4 ± 1.8 | 0.660 | 10.7 ± 1.1 | 9.4 ± 1.7* | 0.241 | 10.4 ± 1.1 | 9.4 ± 1.5 | 0.510 |
| HCT, % | 32.1 ± 4.1 | 29.9 ± 5.6 | 0.706 | 31.3 ± 2.4 | 27.3 ± 5.7 | 0.222 | 30 ± 5.4 | 26 ± 2.4 | 0.243 |
| MCV, fL | 47.2 ± 4.6 | 46.2 ± 5.0 | 0.969 | 46.4 ± 4.0 | 44.7 ± 4.9 | 0.882 | 46.0 ± 5.9 | 44.2 ± 4.7 | 0.858 |
| MCH, pg | 16.3 ± 1.5 | 16.0 ± 1.4 | 0.935 | 15.7 ± 1.3* | 15.4 ± 1.3* | 0.942 | 15.6 ± 1.4 | 15.5 ± 0.9 | 0.991 |
| MCHC, g/dL | 34.7 ± 0.3 | 34.3 ± 0.7 | 0.999 | 34.1 ± 2.6 | 34.7 ± 2.8 | 0.922 | 34.3 ± 3.1 | 35.2 ± 2.9 | 0.857 |
| WBC, ×10³ cells/μL | 11.25 ± 2.4 | 9.7 ± 2.5 | 0.876 | 13.6 ± 5.5 | 12.8 ± 5.0 | 0.980 | 19.8 ± 5.5* | 19.5 ± 4.9* | 0.999 |
| Neutrophils, % | 36.5 ± 11.6 | 26.3 ± 7.1 | 0.108 | 45.4 ± 8.4 | 40.9 ± 8.7* | 0.731 | 40.6 ± 9.1 | 36.9 ± 11.1 | 0.820 |
| Neutrophils, ×10³ cells/μL | 4.13 ± 1.77 | 2.47 ± 0.66 | 0.608 | 6.44 ± 3.87 | 5.41 ± 2.71 | 0.866 | 8.21 ± 3.42 | 7.59 ± 3.83 | 0.967 |
| Lymphocytes, % | 56.7 ± 10.2 | 65.8 ± 6.8 | 0.152 | 47.1 ± 8.2 | 51.0 ± 9.4* | 0.774 | 48.9 ± 9.0 | 54.9 ± 10.7 | 0.485 |
| Lymphocytes, ×10³ cells/μL | 6.37 ± 1.67 | 6.48 ± 2.15 | 0.999 | 6.16 ± 1.56* | 6.34 ± 2.08* | 0.997 | 9.58 ± 2.77 | 10.31 ± 1.45 | 0.853 |
| Monocytes, % | 5.89 ± 1.95 | 6.17 ± 1.19 | 0.981 | 5.74 ± 1.54 | 6.01 ± 2.26 | 0.984 | 8.40 ± 1.95* | 6.80 ± 0.79 | 0.183 |
| Monocytes, cells/μL | 651 ± 241 | 596 ± 193 | 0.985 | 767 ± 283 | 803 ± 517 | 0.996 | 1607 ± 346 | 1336 ± 411 | 0.336 |
| Eosinophils, % | 0.65 ± 0.70 | 1.11 ± 0.56 | 0.587 | 1.45 ± 0.84^ | 1.52 ± 0.78 | 0.997 | 1.67 ± 0.88 | 1.07 ± 0.98 | 0.368 |
| Eosinophils, cells/μL | 65 ± 70 | 108 ± 69 | 0.851 | 203 ± 147* | 213 ± 148 | 0.998 | 310 ± 128 | 179 ± 131 | 0.101 |
| Basophils, % | 0.25 ± 0.21 | 0.57 ± 0.76 | 0.256 | 0.37 ± 0.22 | 0.49 ± 0.28 | 0.912 | 0.35 ± 0.28 | 0.30 ± 0.21 | 0.991 |
| Basophils, cells/μL | 30 ± 28 | 60 ± 81 | 0.539 | 50 ± 33 | 68 ± 51 | 0.861 | 67 ± 49 | 61 ± 41 | 0.994 |
| Neutrophil/ Lymphocyte | 0.70 ± 0.36 | 0.41 ± 0.15 | 0.275 | 1.01 ± 0.35 | 0.85 ± 0.34* | 0.730 | 0.90 ± 0.44 | 0.73 ± 0.34 | 0.689 |

TABLE 7-continued

CBC and blood chemistry analysis of control (n = 8) and
nicotinamide riboside (NR, I) (n = 8) pigs (Mean ± SD)

| | Baseline | | | Wk 1 | | | Wk 2 | | |
|---|---|---|---|---|---|---|---|---|---|
| | Control | NR | P | Control | NR | P | Control | NR | P |
| Blood Chemistry | | | | | | | | | |
| Anion Gap, mmol/L | 28.0 ± 2.0 | 26.7 ± 1.6 | 0.602 | 22.9 ± 2.9* | 21.1 ± 0.9* | 0.438 | 22.9 ± 2.9 | 20.4 ± 1.7 | 0.113 |
| Sodium, mmol/L | 141.1 ± 1.6 | 141.9 ± 0.9 | 0.982 | 131.6 ± 6.7* | 133.1 ± 5.2* | 0.842 | 138.3 ± 2.1* | 137.3 ± 3.5 | 0.952 |
| Potassium, mmol/L | 4.56 ± 0.37 | 4.50 ± 0.23 | 0.997 | 4.46 ± 0.58 | 4.27 ± 0.34 | 0.901 | 4.80 ± 1.09 | 4.10 ± 0.17 | 0.072 |
| Chloride, mmol/L | 99.4 ± 1.5 | 100.3 ± 1.8 | 0.965 | 92.9 ± 6.4* | 96.1 ± 4.4 | 0.300 | 98.1 ± 1.3* | 97.1 ± 4.2 | 0.946 |
| Bicarbonate, mmol/L | 18.4 ± 1.3 | 19.4 ± 1.3 | 0.714 | 20.6 ± 2.4* | 20.1 ± 2.0 | 0.968 | 22.0 ± 2.6 | 23.7 ± 1.6* | 0.288 |
| Phosphorus, mg/dL | 10.1 ± 0.4 | 9.9 ± 0.2 | 0.791 | 6.8 ± 0.5* | 6.5 ± 0.5* | 0.601 | 8.4 ± 0.6* | 7.5 ± 0.8* | 0.011 |
| Calcium, mg/dL | 10.7 ± 0.4 | 10.6 ± 0.3 | 0.999 | 8.9 ± 0.4* | 9.0 ± 0.5* | 0.768 | 9.9 ± 0.3* | 9.8 ± 0.4* | 0.932 |
| BUN, mg/dL | 6.1 ± 3.3 | 5.8 ± 1.6 | 0.995 | 9.0 ± 4.3 | 10.9 ± 2.5* | 0.515 | 8.9 ± 1.9 | 8.6 ± 1.6 | 0.996 |
| Creatinine, mg/dL | 0.93 ± 0.09 | 0.94 ± 0.13 | 0.993 | 1.11 ± 0.16* | 1.07 ± 0.09* | 0.850 | 0.76 ± 0.08* | 0.80 ± 0.08* | 0.850 |
| Glucose, mg/dL | 120.7 ± 8.5 | 117.8 ± 19.4 | 0.968 | 90.1 ± 14.0* | 99.7 ± 6.7* | 0.478 | 70.0 ± 16.1* | 77.1 ± 12.2* | 0.700 |
| Total Protein, g/dL | 4.70 ± 0.28 | 4.59 ± 0.26 | 0.815 | 4.56 ± 0.30 | 4.40 ± 0.27 | 0.626 | 4.59 ± 0.21 | 4.49 ± 0.27 | 0.867 |
| Albumin, g/dL | 3.74 ± 0.33 | 3.74 ± 0.28 | 0.999 | 3.50 ± 0.33^ | 3.43 ± 0.29* | 0.959 | 3.30 ± 0.24 | 3.29 ± 0.30 | 0.999 |
| Globulin, g/dL | 0.96 ± 0.23 | 0.86 ± 0.16 | 0.655 | 1.06 ± 0.08 | 0.97 ± 0.11^ | 0.753 | 1.29 ± 0.29* | 1.20 ± 0.10* | 0.753 |
| AST, U/L | 66.6 ± 50.0 | 45.5 ± 5.8 | 0.632 | 96.1 ± 66.9 | 50.6 ± 26.5 | 0.072 | 31.0 ± 8.7* | 36.7 ± 11.1 | 0.988 |
| Creatine Kinase, ×10$^3$ U/L | 2.82 ± 3.12 | 1.30 ± 0.55 | 0.549 | 3.93 ± 4.72 | 0.88 ± 0.67 | 0.051 | 0.42 ± 0.13* | 0.55 ± 0.30 | 0.999 |
| Alkaline Phosphatase, U/L | 606 ± 254 | 720 ± 213 | 0.438 | 316 ± 80 | 326 ± 45* | 0.999 | 278 ± 80 | 285 ± 66 | 0.999 |
| GGT, U/L | 47.0 ± 9.4 | 43.8 ± 4.3 | 0.739 | 46.6 ± 4.9 | 41.4 ± 6.5 | 0.361 | 50.1 ± 5.8 | 42.6 ± 5.8 | 0.093 |
| Bilirubin Total, mg/dL | 0.51 ± 0.18 | 0.40 ± 0.21 | 0.960 | 0.60 ± 0.31 | 0.40 ± 0.21 | 0.127 | 0.19 ± 0.01 | 0.27 ± 0.10 | 0.820 |

*Significantly different over time with preceding time point;
^Tended different over time with preceding time point Fecal SCFA

TABLE 8

Fecal SCFA in control (n = 8) and nicotinamide riboside (NR, I) (n = 8) pigs (Mean ± SD)

| | Baseline | | | Wk 1 | | | | |
|---|---|---|---|---|---|---|---|---|
| | Control | NR | P | Control | NR | Δ vs. baseline (Control) | Δ vs. baseline (NR) | Significant change from baseline within group |
| Fetal SCFA | | | | | | | | |
| Acetic Acid, ppm | 47.1 ± 17.6 | 43.5 ± 23.5 | 0.999 | 48.5 ± 17.7 | 58.6 ± 14.5 | 1.4 | 15.1 | No |
| Propionic Acid, ppm | 27.3 ± 13.5 | 15.3 ± 10.6 | 0.505 | 38.0 ± 16.8 | 51.2 ± 13.2* | 10.7 | 35.9 | Yes, P < 0.05 |
| Isobutyric Acid, ppm | 7.8 ± 6.3 | 9.5 ± 9.3 | 0.889 | 3.4 ± 6.7 | 6.1 ± 6.4 | -4.4 | -3.4 | No |
| Butyric Acid, ppm | 3.9 ± 8.7 | 11.1 ± 18.4 | 0.635 | 21.2 ± 22.4 | 37.4 ± 16.8* | 17.3 | 26.3 | Yes, P < 0.05 |

TABLE 8-continued

Fecal SCFA in control (n = 8) and nicotinamide riboside (NR, I) (n = 8) pigs (Mean ± SD)

|  | Baseline | | | Wk 1 | | Δ vs. baseline | Δ vs. baseline | Significant change from baseline |
|---|---|---|---|---|---|---|---|---|
|  | Control | NR | P | Control | NR | (Control) | (NR) | within group |
| Isovaleric Acid, ppm | 15.0 ± 8.4 | 16.8 ± 14.0 | 0.962 | 12.1 ± 11.3 | 12.5 ± 9.1 | −2.9 | −4.3 | No |
| Valeric Acid, ppm | 0.6 ± 2.6 | 2.4 ± 6.9 | 0.799 | 5.1 ± 8.9 | 7.8 ± 6.6 | 4.5 | 5.4 | No |

*Significantly different over time with preceding time point

Fecal SCFA Over Two Weeks

TABLE 9

Fecal SCFA in control (n = 8) and nicotinamide riboside (NR, I) (n = 8) pigs (Mean ± SD)

|  | Baseline | | | Wk 1 | | | Wk 1 | | |
|---|---|---|---|---|---|---|---|---|---|
|  | Control | NR | P | Control | NR | P | Control | NR | P |
| Fecal SCFA | | | | | | | | | |
| Acetic Acid, ppm | 47.1 ± 17.6 | 43.5 ± 23.5 | 0.999 | 48.5 ± 17.7 | 58.6 ± 14.5 | 0.999 | 99.2 ± 46.3* | 70.1 ± 62.6 | 0.052 |
| Propionic Acid, ppm | 27.3 ± 13.5 | 15.3 ± 10.6 | 0.505 | 38.0 ± 16.8 | 51.2 ± 13.2* | 0.505 | 94.4 ± 40.8* | 51.5 ± 45.7 | 0.016 |
| Isobutyric Acid, ppm | 7.8 ± 6.3 | 9.5 ± 9.3 | 0.889 | 3.4 ± 6.7 | 6.1 ± 6.4 | 0.832 | 15.3 ± 10.7* | 7.9 ± 10.9 | 0.054 |
| Butyric Acid, ppm | 3.9 ± 8.7 | 11.1 ± 18.4 | 0.635 | 21.2 ± 22.4 | 37.4 ± 16.8* | 0.194 | 76.3 ± 36.7* | 41.2 ± 34.6 | 0.0003 |
| Isovaleric Acid, ppm | 15.0 ± 8.4 | 16.8 ± 14.0 | 0.962 | 12.1 ± 11.3 | 12.5 ± 9.1 | 0.962 | 24.1 ± 17.3* | 11.3 ± 15.7 | 0.021 |
| Valeric Acid, ppm | 0.6 ± 2.6 | 2.4 ± 6.9 | 0.799 | 5.1 ± 8.9 | 7.8 ± 6.6 | 0.765 | 21.6 ± 14.1* | 7.8 ± 11.3 | 0.002 |

*Significantly different over time with preceding time point, p < 0.05

There were no differences in body weight at baseline for the piglets (Table 1), and both groups grew normally over the 2-week intervention as documented by no differences in body weight at either Week 1 or Week 2 of treatment with nicotinamide riboside (NR, I) or control (Table 5). Complete blood count ("CBC") and serum chemistries taken at baseline, and weekly for the 2-week intervention, demonstrated no statistically significant differences between the control piglets and piglets fed nicotinamide riboside (NR, I) (Table 7). Changes over time were expected for growing piglets that are acclimating to a new diet and a new environment away from the sow. See Vladimir Petrovic et al., *The Impact of Suckling and Post-weaning Period on Blood Chemistry of Piglets*, 78 ACTA VETERINARIA BRNO 365 (2009), incorporated by reference herein in its entirety. A comparison to normal references ranges for 6-week-old piglets (Table 2) reveals that the piglets were healthy, with minimal excursions from normal reference ranges, and reveals no differences between control piglets and piglets fed nicotinamide riboside (NR, I). Piglet activity scores indicated that both groups of piglets were alert and attentive (Table 6) and fecal scores were also not statistically different between the control piglets or piglets fed nicotinamide riboside (NR, I), although the group fed nicotinamide riboside (NR, I) had numerically lower fecal scores, indicating softer stools. Together, these findings indicate that feeding nicotinamide riboside (NR, I) did not negatively impact the health, nutritional quality, or normal growth of piglets weaned 7 days early.

Fecal SCFA levels increased in the nicotinamide riboside (NR, I) treaded piglets following 1 week of daily administration of 277 mg of nicotinamide riboside (NR, I) in water. Specifically, marked increases were observed for acetic acid (C2), propionic acid (C3), and butyric acid (C4). The increases were statistically significant for both propionic and butyric acids from baseline to day 7 (Tables 8 and 9). Fecal SCFAs are the products of fermentation of non-digestible carbohydrates and prebiotic substances, by some anaerobic bacteria in the colon. See Gijs den Besten et al., *The role of short-chain fatty acids in the interplay between diet, gut microbiota, and host energy metabolism*, 54 J. LIPID RESEARCH 2325 (2013), incorporated by reference herein in its entirety. Short-chain fatty acids benefit the microbial community by balancing redox equivalent production in the anaerobic environment of the gut, enhancing the growth of beneficial species of bacteria, lactobacilli and bifidobacteria, which are recognized markers of health status, and maintaining gut barrier function. See Milan J. A. van Hoek & Roeland M. H. Merks, *Redox balance is key to explaining full vs. partial switching to low-yield metabolism*, 6 BMC SYSTEMS BIOLOGY 22 (2012); David Rios-Covian et al., *Intestinal short chain fatty acids and their link with diet and human health*, 7 FRONTIERS IN MICROBIOLOGY 185, 2016); each of which is incorporated by reference herein in its entirety. Butyric acid, which was significantly higher than baseline for piglets fed nicotinamide riboside (NR, I) at one week, is the preferred energy source for colonic epithelial cells and has been shown to exert potent anti-inflammatory and immunoregulatory effects. See W. E. W. Roediger, *Role of anaerobic bacteria in the metabolic welfare of the colonic mucosa in man*, 21 GUT 793 (1980); A. Andoh et al., *Physiological and anti-inflammatory roles of dietary fiber and butyrate in intestinal functions*, 23 J. PARENTERAL & ENTERAL NUTRITION S70 (1999); each of which is incorporated by reference herein in its entirety. Beyond the gut, SCFAs have been shown to play a role in protection from obesity and metabolic syndromes, with butyrate and propionate having larger effects than acetate. See Z. Gao et al., *Butyrate improves insulin sensitivity and increases energy expenditure in mice*, 58 DIABETES 1509 (2009), incorporated by reference herein in its entirety. See also Lin, 2012. The observation of significant increases in SCFAs in weanling piglets fed nicotinamide riboside (NR, I) demonstrates the potential to benefit gut and immune system development as well as support optimal development of an infant's microbiome during the critical period of adaptation to infant formula from breastmilk.

The use of the terms "a," "an," "the," and similar referents in the context of describing the presently claimed invention (especially in the context of the claims) are to be construed to cover both the singular and the plural, unless otherwise indicated herein or clearly contracted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately 10%; in other embodiments the values may range in value either above or below the stated value in a range of approximately 5%; in other embodiments the values may range in value either above or below the stated value in a range of approximately 2%; in other embodiments the values may range in value either above or below the stated value in a range of approximately 1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A method for delivering at least one nicotinyl riboside compound, or salt thereof, to an infant mammal subject, comprising the steps of:
    a. providing an infant supplement or nutraceutical composition comprising nicotinamide riboside (NR, I), and optionally at least one nicotinyl riboside compound selected from the group consisting of nicotinic acid riboside (NAR, II), reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and reduced nicotinic acid riboside triacetate (NARH-TA, IX); and
    b. orally administering the infant supplement or nutraceutical composition to the infant mammal subject daily, or every other day, or once a week, or over a period of one or more weeks;
    wherein the amount of nicotinyl riboside compound in the infant supplement or nutraceutical composition is about 1,500 ug to about 10,000 ug per 100 kilocalories of the infant supplement or nutraceutical composition.

2. The method of claim 1, said infant supplement or nutraceutical composition further comprising at least one vitamin selected from the group consisting of vitamin B1 (thiamine, XI), vitamin B2 (riboflavin, XII), and vitamin B6 (pyridoxine, XIII).

3. The method of claim 2, said infant supplement or nutraceutical composition further comprising, for every 300 ug nicotinyl riboside compound in the infant composition, about 40 ug vitamin B1, about 60 ug vitamin B2, and about 35 ug vitamin B6.

4. The method of claim 1, said infant supplement or nutraceutical composition further comprising at least one protein selected from the group consisting of whey and casein.

5. The method of claim 4, wherein said infant supplement or nutraceutical composition is in liquid form; said infant supplement or nutraceutical composition further comprising about 1.8 g-4.5 g protein per 100 kcal infant supplement or nutraceutical composition.

6. The method of claim 5, wherein said nicotinyl riboside compound is nicotinamide riboside (NR, I).

7. The method of claim 1, said infant supplement or nutraceutical composition further comprising calcium, phosphorus, magnesium, zinc, manganese, copper, sodium, potassium, chloride, iron, selenium, chromium, molybdenum, iodine, taurine, carnitine, or choline.

8. The method of claim 1, wherein the mammal is selected from the group consisting of human, horse, pig, and dog.

9. The method of claim 8, wherein the mammal is a human.

10. The method of claim 1, further wherein the level of fecal short chain fatty acid (SCFA) is increased in the mammal.

11. The method of claim 1, wherein said composition further comprises one or more nicotinyl riboside compounds selected from the group consisting of reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and reduced nicotinic acid riboside triacetate (NARH-TA, IX).

12. A method for delivering at least two nicotinyl riboside compounds, or salts thereof, to an infant mammal subject, comprising the steps of:
 a. providing an infant supplement or nutraceutical composition comprising nicotinamide riboside (NR, I), and at least one nicotinyl riboside compound selected from the group consisting of nicotinic acid riboside (NAR, II), reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and reduced nicotinic acid riboside triacetate (NARH-TA, IX); and
 b. orally administering the infant supplement or nutraceutical composition to the infant mammal subject daily, or every other day, or once a week, or over a period of one or more weeks;
  wherein the amount of nicotinyl riboside compound in the infant supplement or nutraceutical composition is about 1,500 ug to about 10,000 ug per 100 kilocalories of the infant supplement or nutraceutical composition.

13. A method for promoting the gut health of an infant mammal subject, comprising the steps of:
 a) providing an infant formula composition comprising nicotinamide riboside (NR, I), and optionally one or more nicotinyl riboside compounds selected from the group consisting of nicotinic acid riboside (NAR, II), reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and reduced nicotinic acid riboside triacetate (NARH-TA, IX); and
 b) orally administering the infant formula composition to the infant mammal subject daily;
  wherein the total amount of the nicotinamide riboside and optional one or more nicotinyl riboside compounds is from about 1,500 ug to about 10,000 ug per 100 kilocalories of the infant formula composition.

14. The method of claim 13, wherein the mammal is selected from the group consisting of human, horse, pig, and dog.

15. The method of claim 14, wherein the mammal is a human.

16. The method of claim 13, wherein the administering step (b) is performed for at least 1 week, and wherein the level of fecal butyric acid increases by at least 25 parts per million following one week of daily administration of the infant formula composition.

17. The method of claim 16, wherein the level of fecal propionic acid increases by at least 35 parts per million following one week of daily administration of the infant formula composition.

18. A method for reducing gastrointestinal inflammation in an infant mammal subject, comprising the steps of:
 a) providing an infant formula composition comprising nicotinamide riboside (NR, I), and optionally one or more nicotinyl riboside compounds selected from the group consisting of nicotinic acid riboside (NAR, II), reduced nicotinamide riboside (NRH, IV), reduced nicotinic acid riboside (NARH, V), nicotinamide riboside triacetate (NRTA, VI), nicotinic acid riboside triacetate (NARTA, VII), reduced nicotinamide riboside triacetate (NRH-TA, VIII), and reduced nicotinic acid riboside triacetate (NARH-TA, IX); and
 b) orally administering the infant formula composition to the infant mammal subject daily;
  wherein the total amount of the nicotinamide riboside and optional one or more nicotinyl riboside compounds is from about 1,500 ug to about 10,000 ug per 100 kilocalories of the infant formula composition.

19. The method of claim 18, wherein the mammal is selected from the group consisting of human, horse, pig, and dog.

20. The method of claim 19, wherein the mammal is a human.

21. The method of claim 18, wherein the level of fecal butyric acid increases by at least 25 parts per million following one week of daily administration of the infant formula composition.

22. The method of claim 21, wherein the administering step (b) is performed for at least 1 week, and wherein the level of fecal propionic acid increases by at least 35 parts per million following one week of daily administration of the infant formula composition.

* * * * *